(12) United States Patent
Darwish et al.

(10) Patent No.: US 8,846,600 B2
(45) Date of Patent: Sep. 30, 2014

(54) CARBOXAMIDE COMPOUNDS AND METHODS FOR USING THE SAME

(71) Applicants: Ihab S. Darwish, San Carlos, CA (US); Hui Hong, Palo Alto, CA (US); Rajinder Singh, Belmont, AZ (US); Xiang Xu, South San Francisco, CA (US)

(72) Inventors: Ihab S. Darwish, San Carlos, CA (US); Hui Hong, Palo Alto, CA (US); Rajinder Singh, Belmont, AZ (US); Xiang Xu, South San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/728,374

(22) Filed: Dec. 27, 2012

(65) Prior Publication Data
US 2013/0131078 A1 May 23, 2013

Related U.S. Application Data

(62) Division of application No. 12/695,861, filed on Jan. 28, 2010, now Pat. No. 8,362,235.

(60) Provisional application No. 61/147,982, filed on Jan. 28, 2009.

(51) Int. Cl.
| | | |
|---|---|---|
| A01N 61/00 | (2006.01) | |
| A61K 31/00 | (2006.01) | |
| A61K 31/497 | (2006.01) | |
| C07D 401/14 | (2006.01) | |
| C07D 401/12 | (2006.01) | |

(52) U.S. Cl.
CPC ............ C07D 401/12 (2013.01); C07D 401/14 (2013.01)
USPC ...................... 514/1; 514/253.09; 514/253.13

(58) Field of Classification Search
USPC ..................................... 514/1, 253.09, 253.13
See application file for complete search history.

(56) References Cited

U.S. PATENT DOCUMENTS

| | | |
|---|---|---|
| 2009/0163511 A1 | 6/2009 | Darwish |
| 2009/0170829 A1 | 7/2009 | Hong |
| 2009/0186894 A1 | 7/2009 | Singh |
| 2009/0275609 A1 | 11/2009 | Yu |
| 2011/0245222 A1 | 10/2011 | Payan |

FOREIGN PATENT DOCUMENTS

| | | |
|---|---|---|
| EP | 1 932 834 | 12/2006 |
| WO | 99/58526 | 11/1999 |

OTHER PUBLICATIONS

Database Registry [Online] Chemical Absracts Service, Columbus, Ohio, US, Registry Nos. 548781-51-7, 548781-09-5 and 548779-43-7 (Jul. 16, 2003); 548468-29-7, 548456-28-6, 548451-66-7, 548440-29-5 and 548437-90-7 (Jul. 15, 2003); 547724-15-2 and 547712-96-9 (Jul. 14, 2003); and 546118-92-7, 546092-83-5, 546092-74-4 and 546082-00-2 (Jul. 11, 2003).
Copending U.S Appl. No. 13/194,810, filed Jul. 29, 2011.
Dorwald, F. A., Side reactions in organic synthesis, 2005, Wiley, VCGH, Weinheim, p. IX of Preface.
Cannon, J. G., Chapter Nineteen in burger's Medicinal Chemistry and Drug Discovery, Fifth Edition, vol. 1: Principles and Practice, Wiley-Interscience, 1995, pp. 783-802.

*Primary Examiner* — Marcos Sznaidman
(74) *Attorney, Agent, or Firm* — Travis Young; McDonnell Boehnen Hulbert & Berghoff LLP

(57) ABSTRACT

Disclosed are carboxamide compounds as well as pharmaceutical compositions and methods of use. One embodiment is a compound having the structure

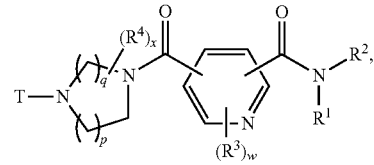

in which $R^1$, $R^2$, $R^3$, $R^4$, T, p, q, w and x are as described herein. In certain embodiments, a compound disclosed herein activates the AMPK pathway, and can be used to treat metabolism-related disorders and conditions.

27 Claims, No Drawings

CARBOXAMIDE COMPOUNDS AND METHODS FOR USING THE SAME

CROSS-REFERENCE TO RELATED APPLICATIONS

This application is a divisional pursuant to 35 U.S.C. §120 of U.S. patent application Ser. No. 12/695,861, filed Jan. 28, 2010, which claims priority under 35 U.S.C. §119(e) to U.S. Provisional Patent Application Ser. No. 61/147,982, filed Jan. 28, 2009, each of which is hereby incorporated herein by reference in its entirety.

BACKGROUND

1. Field

This disclosure relates generally to compounds, pharmaceutical compositions and methods of use of the compounds and compositions containing them. This disclosure relates more particularly to certain carboxamide compounds and pharmaceutical compositions thereof, and to methods of treating and preventing metabolic disorders such as type II diabetes, atherosclerosis and cardiovascular disease using certain carboxamide, sulfonamide and amine compounds.

2. Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the 5"-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis. What is needed are compounds, pharmaceutical compositions and methods of using them to treat disease states associated with circulating adiponectin levels, such as type II diabetes, atherosclerosis and cardiovascular disease.

SUMMARY

Disclosed herein are compounds having structural formula (I)

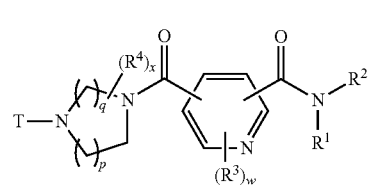

and pharmaceutically acceptable salts, prodrugs and N-oxides thereof (and solvates and hydrates thereof), wherein $R^1$ is H, —($C_1$-$C_4$ alkyl), —C(O)—($C_1$-$C_4$ alkyl) or —C(O)O—($C_1$-$C_4$ alkyl);

$R^2$ is -Hca, -Cak-N($R^9$)-G-$R^{22}$ or —($C_2$-$C_8$ alkyl)-N($R^9$)—$R^{24}$ in which one or two carbons of the ($C_2$-$C_8$ alkyl) are optionally replaced by —O—, —S— or —N($R^9$)— and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

w is 0, 1, 2 or 3;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;

x is 0, 1, 2, 3 or 4;

p is 0, 1, 2, 3 or 4;

q is 2, 3 or 4;

the sum of p and q is 2, 3, 4, 5 or 6;

T is —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$ or

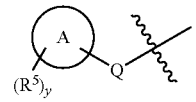

in which

Q is —S(O)$_2$—, L or ($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^6$, R$^7$, R$^8$ and R$^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl), —C(O)—(C$_1$-C$_4$ alkyl) and —C(O)O—(C$_1$-C$_4$ alkyl), each G is independently —S(O)$_2$—, L or —(C$_0$-C$_3$ alkyl)-, in which each carbon of the —(C$_0$-C$_3$ alkyl)- is optionally and independently substituted with one or two R$^{16}$, each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo, each R$^{22}$ and R$^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Also disclosed herein are pharmaceutical compositions. Examples of such compositions include those having at least one pharmaceutically acceptable carrier, diluent or excipient; and a compound, pharmaceutically acceptable salt, prodrug or N-oxide (or solvate or hydrate) described above.

Another aspect of the present disclosure includes methods for modulating metabolism in subjects. Accordingly, also disclosed are methods for treating metabolic disorders using the presently disclosed compounds and pharmaceutical compositions.

Another aspect of the present disclosure includes methods for modulating sphingolipid metabolism, for example modulating ceramide signalling in subjects. In one aspect, modulating sphingolipid metabolism includes modulating ceramidase activity, for example by up-regulating ceramidase function. Accordingly, also disclosed are methods for treating ceramide-linked diseases and disorders using the presently disclosed compounds and pharmaceutical compositions.

DETAILED DESCRIPTION

One aspect of the disclosure provides compounds having structural formula (I):

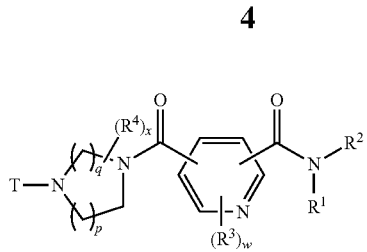

and pharmaceutically acceptable salts, prodrugs and N-oxides thereof (and solvates and hydrates thereof), in which R$^1$ is H, —(C$_1$-C$_4$ alkyl), —C(O)—(C$_1$-C$_4$ alkyl) or —C(O)O—(C$_1$-C$_4$ alkyl);

R$^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and R$^{24}$ is —R$^{23}$, -G-R$^{23}$ or —C(O)O—(C$_1$-C$_6$ alkyl), provided that two consecutive carbons of the (C$_2$-C$_8$ alkyl) are not replaced by —O—;

each R$^3$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each R$^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;

x is 0, 1, 2, 3 or 4;

p is 0, 1, 2, 3 or 4;

q is 2, 3 or 4;

the sum of p and q is 2, 3, 4, 5 or 6;

T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

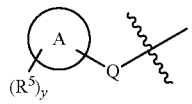

in which

Q is —S(O)$_2$—, L or (C$_0$-C$_3$ alkyl)-, in which each carbon of the —(C$_0$-C$_3$ alkyl)- is optionally and independently substituted with one or two R$^{16}$;

the ring system denoted by "A" is heteroaryl, aryl, cycloalkyl or heterocycloalkyl;

each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$ $C(S)—NR^9—$, $—NR^9C(S)S—$, $—SC(S)NR^9—$, $—NR^9C(S)—$, $—C(S)NR^9—$, $—SC(O)NR^9—$, $—NR^9C(S)—$, $—S(O)_{0-2}—$, $—C(O)O$, $—OC(O)—$, $—C(S)O—$, $—OC(S)—$, $—C(O)S—$, $—SC(O)—$, $—C(S)S—$, $—SC(S)—$, $—OC(O)O—$, $—SC(O)O—$, $—OC(O)S—$, $—SC(S)O—$, $—OC(S)S—$, $—NR^9C(NR^2)NR^9—$, $—NR^9SO_2—$, $—SO_2NR^9—$ and $—NR^9SO_2NR^9—$, each $R^6$, $R^7$, $R^8$ and $R^{10}$ is independently selected from H, $—(C_1-C_6$ alkyl), $—(C_1-C_6$ haloalkyl), $—(C_0-C_6$ alkyl)-Ar, $—(C_0-C_6$ alkyl)-Het, $—(C_0-C_6$ alkyl)-Cak, $—(C_0-C_6$ alkyl)-Hca, $—(C_0-C_6$ alkyl)-L-$(C_0-C_6$ alkyl), $—(C_0-C_6$ alkyl)-NR$^9$-$(C_0-C_6$ alkyl), $—(C_0-C_6$ alkyl)-O—$(C_0-C_6$ alkyl), $—(C_0-C_6$ alkyl)-C(O)—$(C_0-C_6$ alkyl) and $—(C_0-C_6$ alkyl)-S(O)$_{0-2}$—$(C_0-C_6$ alkyl), each $R^9$ is independently selected from $—H$, $—(C_1-C_4$ alkyl), $—C(O)—(C_1-C_4$ alkyl) and $—C(O)O—(C_1-C_4$ alkyl), each G is independently $—S(O)_2—$, L or $—(C_0-C_3$ alkyl)-, in which each carbon of the $—(C_0-C_3$ alkyl)- is optionally and independently substituted with one or two $R^{16}$, each $R^{16}$ is independently selected from $—(C_1-C_6$ alkyl), $—(C_1-C_6$ haloalkyl), $—(C_0-C_6$ alkyl)-Ar, $—(C_0-C_6$ alkyl)-Het, $—(C_0-C_6$ alkyl)-Cak, $—(C_0-C_6$ alkyl)-Hca, $—(C_0-C_6$ alkyl)-L-R$^7$, $—(C_0-C_6$ alkyl)-NR$^8$R$^9$, $—(C_0-C_6$ alkyl)-OR$^{10}$, $—(C_0-C_6$ alkyl)-C(O)R$^{10}$, $—(C_0-C_6$ alkyl)-S(O)$_{0-2}$R$^{10}$, -halogen, $—NO_2$ and $—CN$, and optionally two of $R^{16}$ on the same carbon combine to form oxo.

each $R^{22}$ and $R^{23}$ is independently Ar or Het,
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

In certain embodiments of the presently disclosed compounds of structural formula (I), T is

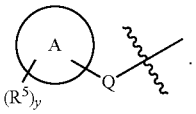

In such embodiments, Q is $—S(O)_2—$, L or $—(C_0-C_3$ alkyl)- in which each carbon of the $(C_0-C_3$ alkyl) is optionally and independently substituted with one or two $R^{16}$, in which each $R^{16}$ is independently selected from $—(C_1-C_6$ alkyl), $—(C_1-C_6$ haloalkyl), $—(C_0-C_6$ alkyl)-Ar, $—(C_0-C_6$ alkyl)-Het, $—(C_0-C_6$ alkyl)-Cak, $—(C_0-C_6$ alkyl)-Hca, $—(C_0-C_6$ alkyl)-L-R$^7$, $—(C_0-C_6$ alkyl)-NR$^8$R$^9$, $—(C_0-C_6$ alkyl)-OR$^{10}$, $—(C_0-C_6$ alkyl)-C(O)R$^{10}$, $—(C_0-C_6$ alkyl)-S(O)$_{0-2}$R$^{10}$, -halogen, $—NO_2$ and $—CN$, and optionally two of $R^{16}$ on the same carbon combine to form oxo. In certain embodiments, each $R^{16}$ is independently selected from $—(C_1-C_6$ alkyl), $—(C_1-C_6$ haloalkyl) (e.g., difluoromethyl, trifluoromethyl and the like), $—(C_0-C_6$ alkyl)-L-R$^7$, $—(C_0-C_6$ alkyl)-NR$^8$R$^9$, $—(C_0-C_6$ alkyl)-OR$^{10}$, $—(C_0-C_6$ alkyl)-C(O)R$^{10}$, $—(C_0-C_6$ alkyl)-S(O)$_{0-2}$R$^{10}$, -halogen, $—NO_2$ and $—CN$, and two $R^{16}$ on the same carbon optionally combine to form an oxo, in which each $R^7$, $R^8$ and $R^{10}$ is independently selected from H, $—(C_1-C_6$ alkyl), $—(C_1-C_6$ haloalkyl), $—(C_0-C_6$ alkyl)-L-$(C_0-C_6$ alkyl), $—(C_0-C_6$ alkyl)-NR$^9$($C_0-C_6$ alkyl), $—(C_0-C_6$ alkyl)-O—$(C_0-C_6$ alkyl), $—(C_0-C_6$ alkyl)-C(O)—$(C_0-C_6$ alkyl), and $—(C_0-C_6$ alkyl)-S(O)$_{0-2}$—$(C_0-C_6$ alkyl), and in which no alkyl or haloalkyl is substituted with an aryl-, heteroaryl-, cycloalkyl- or heterocycloalkyl-containing group. For example, in particular compounds, each $R^{16}$ is $—(C_1-C_3$ alkyl), $—(C_1-C_3$ haloalkyl), $—(C_0-C_3$ alkyl)-L-R$^7$, $—(C_0-C_3$ alkyl)-NR$^8$R$^9$, $—(C_0-C_3$ alkyl)-OR$^{10}$, $—(C_0-C_3$ alkyl)-C(O)R$^{10}$, $—(C_0-C_3$ alkyl)-S(O)$_{0-2}$R$^{10}$, -halogen, $—NO_2$ and $—CN$, and two $R^{16}$ on the same carbon optionally combine to form an oxo, in which each $R^7$, $R^8$ and $R^{10}$ is independently selected from H, $—(C_1-C_2$ alkyl), $—(C_1-C_2$ haloalkyl), $—(C_0-C_2$ alkyl)-L-$(C_0-C_2$ alkyl), $—(C_0-C_2$ alkyl)-NR$^9$($C_0$-$C_2$ alkyl), $—(C_0-C_2$ alkyl)-O—$(C_0-C_2$ alkyl), $—(C_0-C_2$ alkyl)-C(O)—$(C_0-C_2$ alkyl) and $—(C_0-C_2$ alkyl)-S(O)$_{0-2}$—$(C_0-C_2$ alkyl), and in which no alkyl or haloalkyl is substituted with an aryl-, heteroaryl-, cycloalkyl- or heterocycloalkyl-containing group. In certain embodiments, Q has at most one $R^{16}$ or an oxo substituted thereon. Q can be, for example, an unsubstituted $—(C_0-C_3$ alkyl)-. In other embodiments, Q is a $(C_1-C_3$ alkyl) having as its only substitution a single oxo group. For example, in certain embodiments, Q is $—CH—$; a single bond; $—S(O)_2—$; $—C(O)—$; or $—CH(CH_3)—$.

In certain embodiments of the compounds of structural formula (I), the

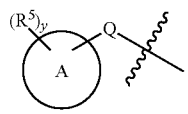

moiety is

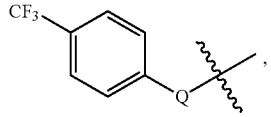

for example, p-(trifluoromethyl)phenyl. In other embodiments, the

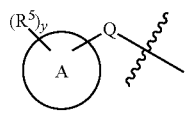

moiety is

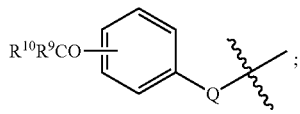

in one such embodiment, Q is a single bond.

The number of substituents on the ring system denoted by "A", y, is 0, 1, 2, 3 or 4. For example, in some embodiments of the presently disclosed compounds of structural formula (I), y is 0, 1, 2 or 3, such as 1. In one embodiment, y is not zero and at least one $R^5$ is halo, cyano, $—(C_1-C_4$ haloalkyl), $—O—(C_1-C_4$ haloalkyl), $—(C_1-C_4$ alkyl), $—O—(C_1-C_4$ alkyl), $—C(O)—(C_0-C_4$ alkyl), $—C(O)O—(C_0-C_4$ alkyl), $—C(O)N$ $(C_0-C_4$ alkyl)$(C_0-C_4$ alkyl), $NO_2$ or —C(O)—Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (I), each $R^5$ is independently selected from —$(C_1-C_6$ alkyl), —$(C_1-C_6$ haloalkyl) (e.g., difluoromethyl, trifluoromethyl and the like), —$(C_0-C_6$—$(C_0-C_6$ alkyl)-$NR^8R^9$, —$(C_0-C_6$ alkyl)-$OR^{10}$, —$(C_0-C_6$ alkyl)-C(O)$R^{10}$, —$(C_0-C_6$ alkyl)-$S(O)_{0-2}R^{10}$, -halogen, —$NO_2$ and —CN, in which each $R^7$, $R^8$ and $R^{10}$ is independently selected from H, —$(C_1-C_6$ alkyl), —$(C_1-C_6$ haloalkyl) (e.g., difluoromethyl, trifluoromethyl and the like), —$(C_0-C_6$ alkyl)-L-$(C_0-C_6$ alkyl), —$(C_0-C_6$ alkyl)-$NR^9(C_0-C_6$ alkyl), —$(C_0-C_6$ alkyl)-O—$(C_0-C_6$ alkyl), —$(C_0-C_6$ alkyl)-C(O)—$(C_0-C_6$ alkyl) and —$(C_0-C_6$ alkyl)-$S(O)_{0-2}$—$(C_0-C_6$ alkyl), and in which no alkyl or haloalkyl is substituted with an aryl-, heteroaryl-, cycloalkyl- or heterocycloalkyl-containing group. For example, in one embodiment, each $R^5$ is —$(C_1-C_3$ alkyl), —$(C_1-C_3$ haloalkyl), —$(C_0-C_3$ alkyl)-L-$R^7$, —$(C_0-C_3$ alkyl)-$NR^8R^9$, —$(C_0-C_3$ alkyl)-$OR^{10}$, —$(C_0-C_3$ alkyl)-C(O)$R^{10}$, —$(C_0-C_3$ alkyl)-$S(O)_{0-2}R^{10}$, -halogen, —$NO_2$ and —CN, in which each $R^7$, $R^8$ and $R^{10}$ is independently selected from H, —$(C_1-C_2$ alkyl), —$(C_1-C_2$ haloalkyl), —$(C_0-C_2$ alkyl)-L-$(C_0-C_2$ alkyl), —$(C_0-C_2$ alkyl)-$NR^9(C_0-C_2$ alkyl), —$(C_0-C_2$ alkyl)-O—$(C_0-C_2$ alkyl), —$(C_0-C_2$ alkyl)-C(O)—$(C_0-C_2$ alkyl) and —$(C_0-C_2$ alkyl)-$S(O)_{0-2}$—$(C_0-C_2$ alkyl), and in which no alkyl or haloalkyl is substituted with an aryl-, heteroaryl-, cycloalkyl- or heterocycloalkyl-containing group.

In one embodiment of the compounds of structural formula (I), y is 0.

In the presently disclosed compounds of structural formula (I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —$(C_0-C_3$ alkyl)- optionally substituted with oxo, and optionally substituted with one or more $R^{16}$. For example, Q can be a —$(C_1-C_3$ alkyl)- having its only substitution a single oxo, or an unsubstituted —$(C_0-C_3$ alkyl)-. For example, in certain embodiments, Q is —$CH_2$—; a single bond; —$S(O)_2$—; —C(O)—; or —$CH(CH_3)$—.

For example, in certain embodiments of the presently disclosed compounds of structural formula (I), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —$(C_1-C_4$ haloalkyl), —O—$(C_1-C_4$ haloalkyl), —$(C_1-C_4$ alkyl), —O—$(C_1-C_4$ alkyl), —C(O)—$(C_0-C_4$ alkyl), —C(O)O—$(C_0-C_4$ alkyl), —C(O)N$(C_0-C_4$ alkyl)$(C_0-C_4$ alkyl), $NO_2$ and —C(O)—Hca in which the Hca contains a ring nitrogen atom through which it is bound to the —C(O)—, and in which no $(C_0-C_4$ alkyl) or $(C_1-C_4$ alkyl) is substituted by an aryl, heteroaryl, cycloalkyl or heterocycloalkyl-containing group. $R^5$ can be, for example, —Cl, —F, cyano, —C(O)$CH_3$, —C(O)OH, —C(O)$NH_2$, trifluoromethyl, difluoromethyl, difluoromethoxy or trifluoromethoxy. In another embodiment, the

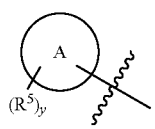

moiety is a 3,4-dihalophenyl.

In another embodiment of the presently disclosed compounds of structural formula (I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —$(C_0-C_3$ alkyl)- optionally substituted with oxo, and optionally substituted with one or more $R^{16}$. For example, Q can be a —$(C_1-C_3$ alkyl)- having its only substitution a single oxo, or an unsubstituted —$(C_0-C_3$ alkyl)-. In certain embodiments, Q is —$CH_2$—; a single bond; —$S(O)_2$—; —C(O)—; or —$CH(CH_3)$—.

In one embodiment of the presently disclosed compounds, the compound has structural formula (II):

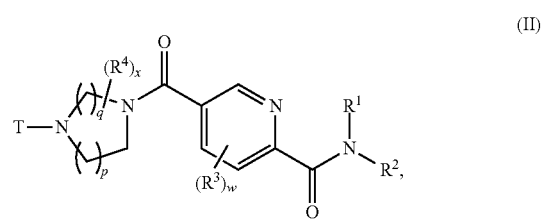

(II)

in which the variables are defined as described above with reference to structural formula (I).

In one embodiment of the presently disclosed compounds, the compound has structural formula (III):

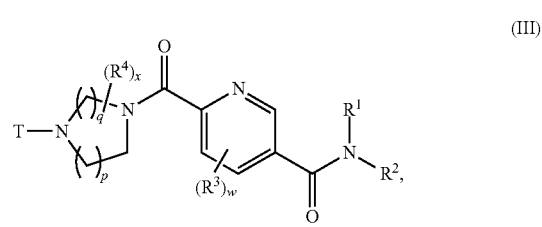

(III)

in which the variables are defined as described above with reference to structural formula (I).

In another embodiment of the presently disclosed compounds, the compound has structural formula (IV):

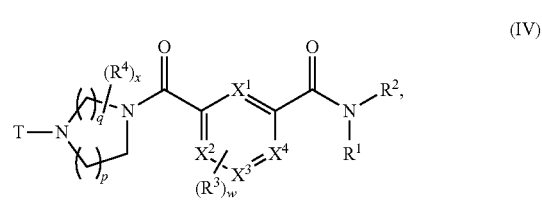

(IV)

in which one of $X^1$, $X^2$, $X^3$ and $X^4$ are N, and the others are carbons (for example, independently CH or C substituted with one of the w $R^3$ groups), and all other variables are defined as described above with reference to structural formula (I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In compounds according to structural formulae (I)-(IV), p is 0, 1, 2, 3 or 4 and q is 2, 3 or 4. For example, in one embodiment, q is 2. In certain embodiments, p is 1.

In certain embodiments according to structural formulae (I)-(IV), the sum of p and q is 2 or 3. For example, in one embodiment, the sum of p and q is 2 (e.g., p is 0 and q is 2). In another embodiment, the sum of p and q is 3 (e.g., p is 1 and q is 2). In other embodiments the sum of p and q is 4, 5, or 6. Accordingly the ring containing the p and q carbon atoms can be a 5, 6, 7, 8 or 9-membered ring.

In one embodiment of the presently disclosed compounds, the compound has the structural formula (V):

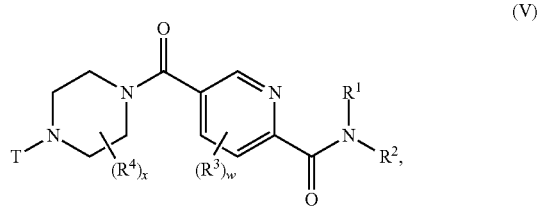

(V)

in which the variables are defined as described above with reference to structural formula (I).

In another embodiment of the presently disclosed compounds, the compound has structural formula (VI):

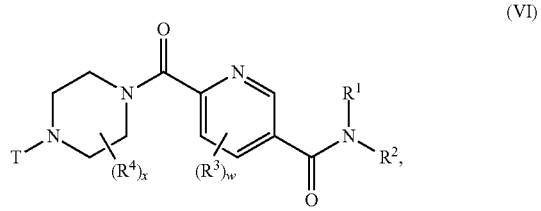

(VI)

in which the variables are defined as described above with reference to structural formula (I).

In another embodiment of the presently disclosed compounds, the compound has structural formula (VII):

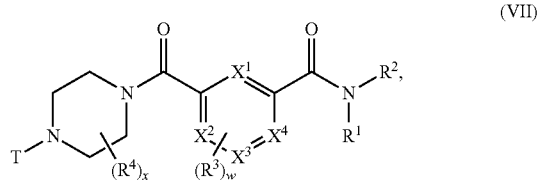

(VII)

in which one of $X^1$, $X^2$, $X^3$ and $X^4$ are N, and the others are carbons (for example, independently CH or C substituted with one of the w $R^3$ groups), and all other variables are defined as described above with reference to structural formula (I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In certain embodiments of the presently disclosed compounds of any of structural formulae (I)-(VII), $R^1$ is —H. In other embodiments, $R^1$ is ($C_1$-$C_4$ alkyl), for example methyl, ethyl, n-propyl or isopropyl. In still other embodiments, $R^1$ is —C(O)—O—($C_1$-$C_4$ alkyl), for example —C(O)—O-t-butyl. In certain embodiments, no alkyl of $R^1$ is substituted with an aryl-, heteroaryl-, cycloalkyl- or heterocycloalkyl-containing group.

In certain embodiments of the presently disclosed compounds of any structural formulae (I)-(VII), $R^2$ is -Hca. In certain embodiments, $R^2$ is an optionally-substituted monocyclic heterocycloalkyl. In one embodiment, $R^2$ is not an oxo-substituted heterocycloalkyl.

In certain of the presently disclosed compounds of any structural formulae (I)-(VII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (I)-(VII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (I)-(VII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (I)-(VII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (I)-(VII), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—$NR^9$—, such as —C(O)—NH—.

In other embodiments of the presently disclosed compounds of any of structural formulae (I)-(VII), the azetidinyl, pyrrolidinyl, piperidinyl or azepanyl $R^2$ moiety is substituted at its 1-position with —C(O)—O($C_0$-$C_6$ alkyl), —C(O)—Het, —C(O)—Ar, —S(O)$_2$-Het, —S(O)$_2$—Ar or —S(O)$_2$—O($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)—Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments of the compounds of any of structural formulae (I)-(VII), $R^2$ is -Cak-N($R^9$)-G-$R^{22}$, as described above. For example, in one embodiment of the disclosed compounds, $R^2$ has the structure

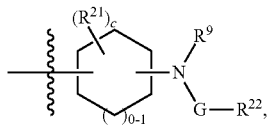

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, each $R^{22}$ is not substituted with an aryl-, heteroaryl-, cycloalkyl- or heterocycloalkyl-containing group. In certain embodiments of the presently disclosed compounds, each $R^{23}$ is not substituted with an aryl-, heteroaryl-, cycloalkyl- or heterocycloalkyl-containing group.

In one embodiment of compounds of any of structural formulae (I)-(VII), $R^2$ has the structure

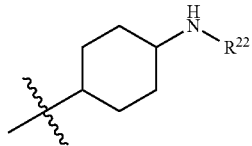

In certain embodiments of the compounds of any of structural formulae (I)-(VII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -$GR^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$; or —$CH_2$—$CH_2$—$CH_2$—$CH_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CH_2$—CH($CH_3$)—N($R^9$)—$R^{24}$; or —$CH_2$—$CH_2$—O—$CH_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In the compounds of any of structural formulae (I)-(VII), the number of substituents on the central pyridine, w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the central pyridine in the meta position relative to the carbonyl bearing the diazacycloalkyl moiety.

In certain embodiments of the compounds of any of structural formulae (I)-(VII), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of any of structural formulae (I)-(VII), w is at least one, and at least one $R^3$ is —$NR^8R^9$. For example, in one embodiment, w is 1. In certain such embodiments, an $R^3$ is substituted on the central pyridine in the meta position relative to the carbonyl bearing the diazacycloalkyl moiety.

In other embodiments of the compounds of any of structural formulae (I)-(VII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the central pyridine in the meta position relative to the carbonyl bearing the diazacycloalkyl moiety. In one particular embodiment, $R^3$ is —$CH_2$—N($CH_3$)—$CH_2$—C(O)—$OCH_3$.

In the presently disclosed compounds of any of structural formulae (I)-(VII), the number of substituents on the diazacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (I)-(VII), two $R^4$ groups combine to form an oxo. The oxo can be bound, for example, at the position alpha to a nitrogen of the diazacycloalkyl ring. In other embodiments, no two $R^4$ groups combine to form an oxo.

In certain embodiments of the presently disclosed compounds of any of structural formulae (I)-(VII), when x is 4, not all four $R^4$ groups are ($C_1$-$C_6$ alkyl).

In certain embodiments of the presently disclosed compounds of any of structural formulae (I)-(VII), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (VIII):

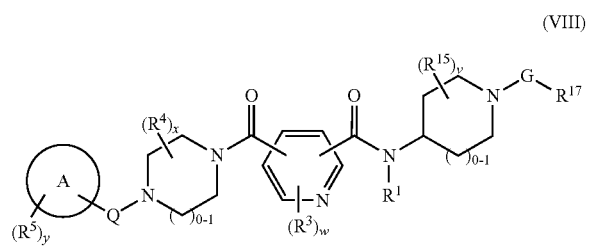

(VIII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (I)-(VII). In one embodiment, Q is a single bond. In another embodiment, Q is —$CH_2$—. In other embodiments, Q is —C(O)— or —S(O)$_2$—. In certain embodiments, G is —$CH_2$—. In other embodiments, G is —C(O)— or —S(O)$_2$—. In other embodiments, G is —CH($CH_3$)—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (VIII), v is 0, 1, 2, 3 or 4. In one embodiment, v is 0, 1, 2 or 3. For example, v can be 0, or can be 1 or 2.

In certain embodiments of the presently disclosed compounds of structural formula (VIII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (VIII), when v is 4, not all four $R^{15}$ moieties are $(C_1-C_6$ alkyl).

In certain embodiments of the presently disclosed compounds of structural formula (VIII), each $R^{15}$ is independently selected from $—(C_1-C_6$ alkyl), $—(C_1-C_6$ haloalkyl) (e.g., difluoromethyl, trifluoromethyl and the like), $—(C_0-C_6$ alkyl)-L-$R^7$, $—(C_0-C_6$ alkyl)-$NR^8R^9$, $—(C_0-C_6$ alkyl)-$OR^{10}$, $—(C_0-C_6$ alkyl)-$C(O)R^{10}$—, $—(C_0-C_6$ alkyl)-$S(O)_{0-2}R^{10}$, -halogen, $—NO_2$ and $—CN$ and two $R^{15}$ on the same carbon optionally combine to form oxo, in which each $R^7$, $R^8$ and $R^{10}$ is independently selected from H, $—(C_1-C_6$ alkyl), $—(C_1-C_6$ haloalkyl), $—(C_0-C_6$ alkyl)-L-$(C_0-C_6$ alkyl), $—(C_0-C_6$ alkyl)-$NR^9(C_0-C_6$ alkyl), $—(C_0-C_6$ alkyl)-O—$(C_0-C_6$ alkyl), $—(C_0-C_6$ alkyl)-C(O)—$(C_0-C_6$ alkyl) and $—(C_0-C_6$ alkyl)-S$(O)_{0-2}$—$(C_0-C_6$ alkyl), and in which no alkyl or haloalkyl is substituted with an aryl-, heteroaryl-, cycloalkyl- or heterocycloalkyl-containing group. For example, in one embodiment, each $R^{15}$ is $—(C_1-C_3$ alkyl), $—(C_1-C_3$ haloalkyl), $—(C_0-C_3$ alkyl)-L-$R^7$, $—(C_0-C_3$ alkyl)-$NR^8R^9$, $—(C_0-C_3$ alkyl)-$OR^{10}$, $—(C_0-C_3$ alkyl)-$C(O)R^{10}$, $—(C_0-C_3$ alkyl)-$S(O)_{0-2}R^{10}$, -halogen, $—NO_2$ and $—CN$ and two $R^{15}$ on the same carbon optionally combine to form oxo, in which each $R^7$, $R^8$ and $R^{10}$ is independently selected from H, $—(C_1-C_2$ alkyl), $—(C_1-C_2$ haloalkyl), $—(C_0-C_2$ alkyl)-L-$(C_0-C_2$ alkyl), $—(C_0-C_2$ alkyl)-$NR^9(C_0-C_2$ alkyl), $—(C_0-C_2$ alkyl)-O—$(C_0-C_2$ alkyl), $—(C_0-C_2$ alkyl)-C(O)—$(C_0-C_2$ alkyl) and $—(C_0-C_2$ alkyl)-S$(O)_{0-2}$—$(C_0-C_2$ alkyl), and in which no alkyl or haloalkyl is substituted with an aryl-, heteroaryl-, cycloalkyl- or heterocycloalkyl-containing group. In some embodiments, one $R^{15}$ is $—C(O)NR^9R^7$, which can be bound, for example, at a position alpha relative to the piperidine nitrogen, or at the position linked to the $—N(R^1)—$.

In certain embodiments of the presently disclosed compounds of structural formula (VIII), $R^{17}$ is an unsubstituted aryl or heteroaryl. In other embodiments, the $R^{17}$ Ar or Het is substituted with 1, 2 or 3 substituents independently selected from $—(C_1-C_6$ alkyl), $—(C_1-C_6$ haloalkyl) (e.g., difluoromethyl, trifluoromethyl and the like), $—(C_0-C_6$ alkyl)-L-$R^7$, $—(C_0-C_6$ alkyl)-$NR^8R^9$, $—(C_0-C_6$ alkyl)-$OR^{10}$, $—(C_0-C_6$ alkyl)-$C(O)R^{10}$, $—(C_0-C_6$ alkyl)-$S(O)_{0-2}R^{10}$, -halogen, $—NO_2$ and $—CN$, in which each $R^7$, $R^8$ and $R^{10}$ is independently selected from H, $—(C_1-C_6$ alkyl), $—(C_1-C_6$ haloalkyl), $—(C_0-C_6$ alkyl)-L-$(C_0-C_6$ alkyl), $—(C_0-C_6$ alkyl)-$NR^9(C_0-C_6$ alkyl), $—(C_0-C_6$ alkyl)-O—$(C_0-C_6$ alkyl), $—(C_0-C_6$ alkyl)-C(O)—$(C_0-C_6$ alkyl) and $—(C_0-C_6$ alkyl)-S$(O)_{0-2}$—$(C_0-C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from $—(C_1-C_3$ alkyl), $—(C_1-C_3$ haloalkyl), $—(C_0-C_3$ alkyl)-L-$R^7$, $—(C_0-C_3$ alkyl)-$NR^8R^9$, $—(C_0-C_3$ alkyl)-$OR^{10}$, $—(C_0-C_3$ alkyl)-$C(O)R^{10}$, $—(C_0-C_3$ alkyl)-$S(O)_{0-2}R^{10}$, -halogen, $—NO_2$ and $—CN$, in which each $R^7$, $R^8$ and $R^{10}$ is independently selected from H, $—(C_1-C_2$ alkyl), $—(C_1-C_2$ haloalkyl), $—(C_0-C_2$ alkyl)-L-$(C_0-C_2$ alkyl), $—(C_0-C_2$ alkyl)-$NR^9(C_0-C_2$ alkyl), $—(C_0-C_2$ alkyl)-O—$(C_0-C_2$ alkyl), $—(C_0-C_2$ alkyl)-C(O)—$(C_0-C_2$ alkyl) and $—(C_0-C_2$ alkyl)-S$(O)_{0-2}$—$(C_0-C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, $—(C_1-C_4$ haloalkyl), $—O—(C_1-C_4$ haloalkyl), $—(C_1-C_4$ alkyl), $—O—(C_1-C_4$ alkyl), $—C(O)—(C_0-C_4$ alkyl), $—C(O)O—(C_0-C_4$ alkyl), $—C(O)N(C_0-C_4$ alkyl)$(C_0-C_4$ alkyl), $NO_2$ and $—C(O)$—Hca. $R^{17}$ can be substituted with, for example, one such substituent, or two such substituents.

In certain embodiments, the presently disclosed compounds have the structural formula (IX):

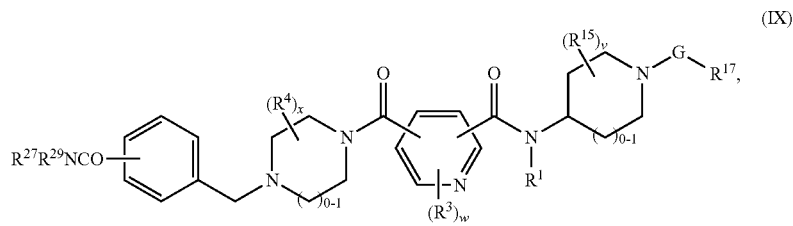

(IX)

in which $R^{27}$ is selected from H, $—(C_1-C_6$ alkyl), $—(C_1-C_6$ haloalkyl) (e.g., difluoromethyl, trifluoromethyl and the like), $—(C_0-C_6$ alkyl)-L-$(C_0-C_6$ alkyl), $—(C_0-C_6$ alkyl)-$NR^9(C_0-C_6$ alkyl), $—(C_0-C_6$ alkyl)-O—$(C_0-C_6$ alkyl), $—(C_0-C_6$ alkyl)-C(O)—$(C_0-C_6$ alkyl)-$(C_0-C_6$ alkyl)-S$(O)_{0-2}$—$(C_0-C_6$ alkyl), in which no heterocycloalkyl, alkyl or haloalkyl is substituted with an aryl-, heteroaryl-, cycloalkyl- or heterocycloalkyl-containing group, and $R^{29}$ is —H, $—(C_1-C_4$ alkyl), $—C(O)$—$(C_1-C_4$ alkyl) or $—C(O)$—O—$(C_1-C_4$ alkyl) in which no $(C_1-C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H.

In certain embodiments, the presently disclosed compounds have the structural formula (X):

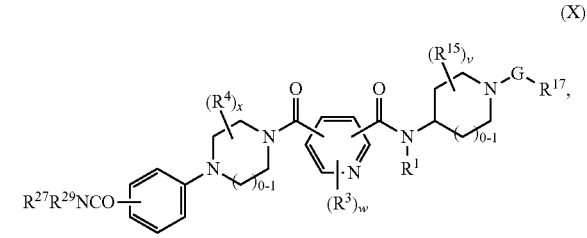

(X)

in which $R^{27}$ is selected from H, $—(C_1-C_6$ alkyl), $—(C_1-C_6$ haloalkyl) (e.g., difluoromethyl, trifluoromethyl and the like), $—(C_0-C_6$ alkyl)-L-$(C_0-C_6$ alkyl), $—(C_0-C_6$ alkyl)-$NR^9(C_0-C_6$ alkyl), $—(C_0-C_6$ alkyl)-O—$(C_0-C_6$ alkyl), $—(C_0-C_6$ alkyl)-C(O)—$(C_0-C_6$ alkyl)-$(C_0-C_6$ alkyl)-S$(O)_{0-2}$—$(C_0-C_6$ alkyl), in which no heterocycloalkyl, alkyl or haloalkyl is substituted with an aryl-, heteroaryl-, cycloalkyl- or heterocycloalkyl-containing group, and $R^{29}$ is —H, $—(C_1-C_4$ alkyl), $—CO—O—(C_1-C_4$ alkyl) or $—CO—O—(C_1-C_4$ alkyl) in which no $(C_1-C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H.

In certain embodiments, the presently disclosed compounds have the structural formula (XI):

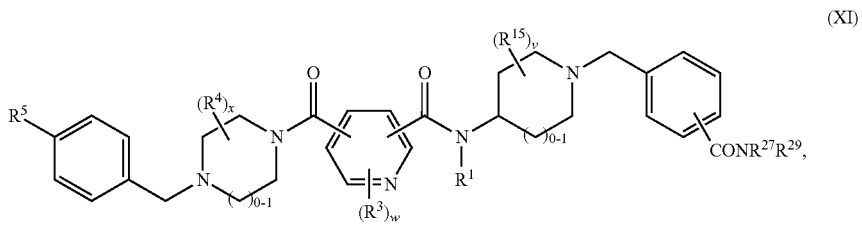

(XI)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H.

In certain embodiments, the presently disclosed compounds have the structural formula (XII):

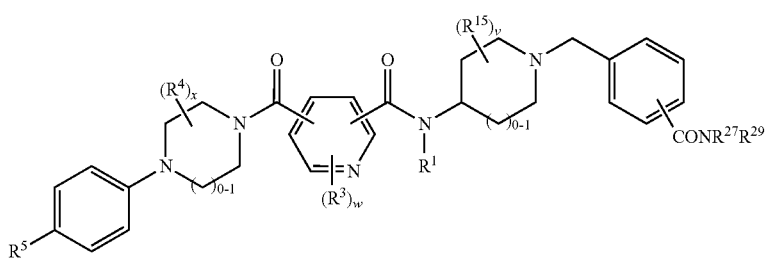

(XII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H.

In certain embodiments, the presently disclosed compounds have the structural formula (XIII):

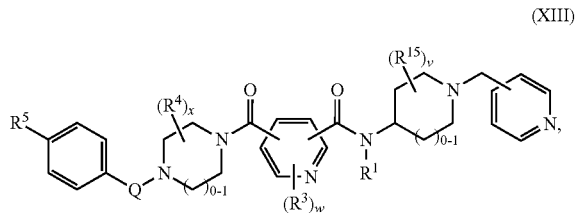

(XIII)

in which all variables are as described above with reference to any of structural formulae (I)-(VIII).

In certain embodiments, the presently disclosed compounds have the structural formula (XIV):

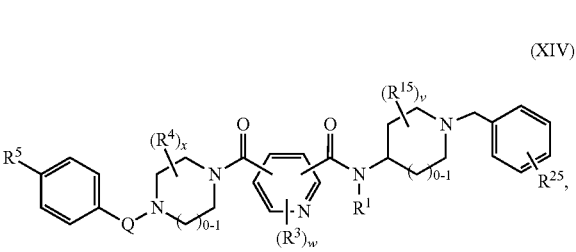

(XIV)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (I)-(VIII). $R^{25}$ can be, for example, —Cl, —F, cyano, —C(O)CH$_3$, —C(O)OH, —C(O)NH$_2$, trifluoromethyl, difluoromethyl, difluoromethoxy or trifluoromethoxy.

In certain embodiments, the presently disclosed compounds have the structural formula (XV):

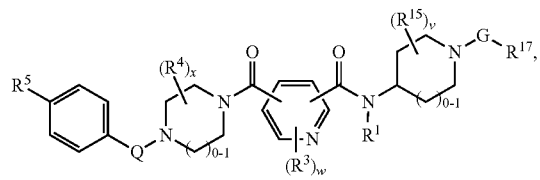

(XV)

in which G is —C(O)—, —S(O)$_2$— or —C(O)—NH— and all other variables are as described above with reference to any of structural formulae (I)-(VIII).

In certain embodiments, the presently disclosed compounds have the structural formula (XVI):

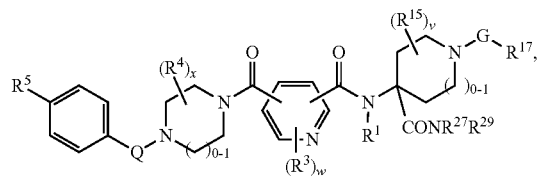

(XVI)

in which $R^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and $R^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H. In some embodiments, the compounds of structural formula (VIII) are present as racemic mixtures or scalemic mixtures. In other embodiments, the compounds of structural formula (XVI) are present in an enantiomerically-enriched form, for example as a substantially pure stereoisomer.

In certain embodiments, the presently disclosed compounds have the structural formula (XVII):

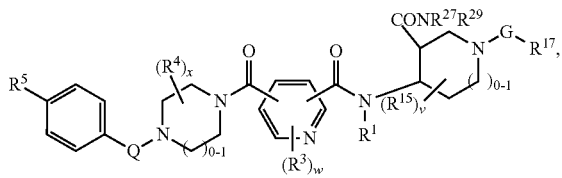

(XVII)

in which $R^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and $R^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(VIII). In one embodiment, $R^{27}$ and $R^{29}$ are both H. In some embodiments, the compounds of structural formula (VIII) are present as racemic mixtures or scalemic mixtures. In other embodiments, the compounds of structural formula (XVII) are present in an enantiomerically-enriched form, for example as a substantially pure stereoisomer.

In certain embodiments, the presently disclosed compounds have the structural formula (XVIII):

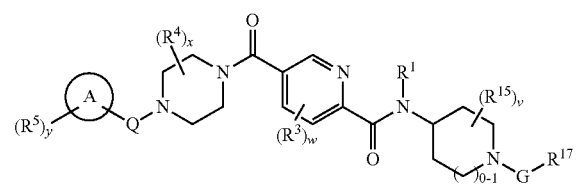

(XVIII)

in which G, v, $R^{15}$ and $R^{17}$ are defined as described above with reference to structural formula (VIII), and all other variables are defined as described above with reference to structural formulae (I) or (II). $R^5$, y, v, $R^{15}$, $R^{17}$, Q, G and the ring denoted by "A" can be defined, for example, as described with reference to any of structural formulae (IX)-(XVII).

In certain embodiments, the presently disclosed compounds have the structural formula (XIX):

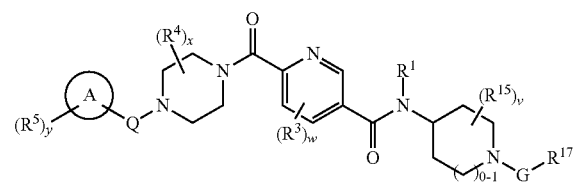

(XIX)

in which G, v, $R^{15}$ and $R^{17}$ are defined as described above with reference to structural formula (VIII), and all other variables are defined as described above with reference to structural formulae (I) or (III). $R^5$, y, v, $R^{15}$, $R^{17}$, Q, G and the ring denoted by "A" can be defined, for example, as described with reference to any of structural formulae (IX)-(XVII).

In certain embodiments, the presently disclosed compounds have the structural formula (XX):

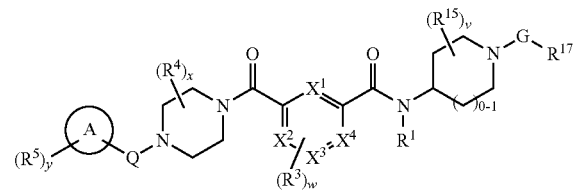

(XX)

in which one of $X^1$, $X^2$, $X^3$ and $X^4$ are N, and the others are carbons (for example, independently CH or C substituted with one of the w $R^3$ groups), as described above with reference to structural formulae (IV) and (VII); G, v, $R^{15}$ and $R^{17}$ are defined as described above with reference to structural formula (VIII), and all other variables are defined as described above with reference to structural formulae (I) or (IV). $R^5$, y, v, $R^{15}$, $R^{17}$, Q, G and the ring denoted by "A" can be defined, for example, as described with reference to any of structural formulae (IX)-(XVII).

In certain embodiments of compounds having structural formulae (VIII)-(XX), the

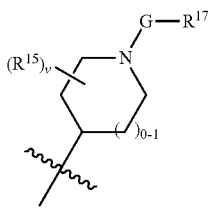

moiety has the structure

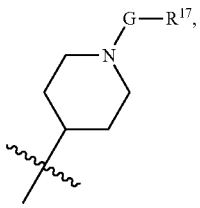

in which G is —$CH_2$—, —$CH(CH_3)$—, —C(O)—, —$S(O)_2$— or —C(O)—NH—. For example, in one embodiment, G is —$CH_2$—. In another embodiment, G is —C(O)— or —$S(O)_2$—. In another embodiment, G is —C(O)—NH—.

In other embodiments of compounds having structural formulae (VIII)-(XX), the

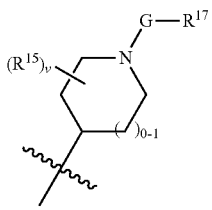

moiety has the structure

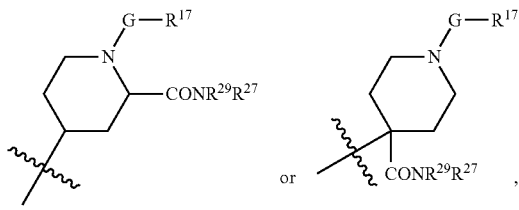

in which G is —$CH_2$—, —C(O)—, —$S(O)_2$— or —C(O)—NH—, $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (VIII)-(XX), the

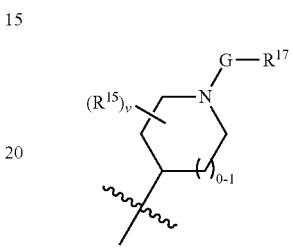

moiety has the structure

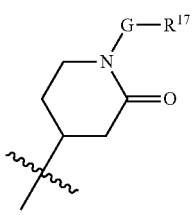

in which G is —$CH_2$—, —C(O)—, —$S(O)_2$— or —C(O)—NH—.

In certain embodiments of compounds having structural formulae (VIII)-(XX), the $R^{17}$ moiety has the structure

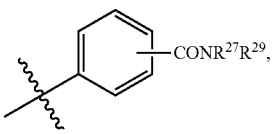

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

In certain embodiments of compounds having structural formulae (VIII)-(XX), w is 1, and $R^3$ is —$NR^8R^9$. In certain such embodiments, $R^3$ is substituted on the central pyridine in a meta position relative to the —C(O)— bearing the diazacycloalkyl moiety.

In other embodiments of compounds having structural formulae (VIII)-(XX), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted on the central pyridine in a meta position relative to the —C(O)— bearing the diazacycloalkyl moiety.

In certain embodiments described above, each $R^{27}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group, and each $R^{29}$ is H, methyl or ethyl, or $R^{27}$ and $R^{29}$ together with the nitrogen to which they are bound form Hca.

In certain embodiments of compounds having structural formulae (VIII)-(XX), at least one $R^5$ moiety is a haloalkyl group, and in exemplary embodiments of these formulae the

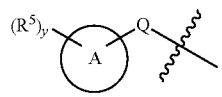

moiety is p-(trifluoromethyl)phenyl, p-fluorophenyl or p-cyanophenyl. By way of further illustration, certain exemplary compounds including such

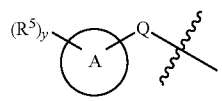

moieties have structural formula (XXI), (XXII) or (XXIII):

(XXI)

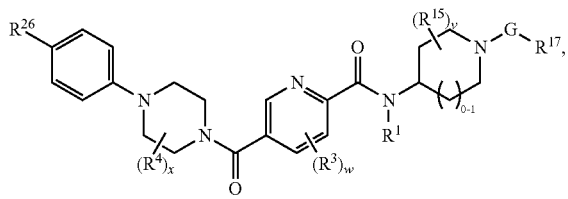

(XXII)

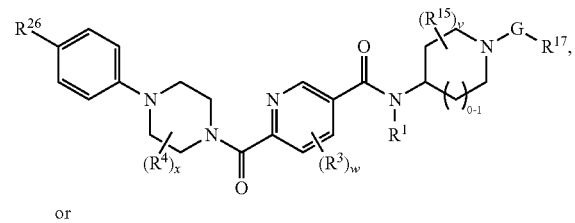

or (XXIII)

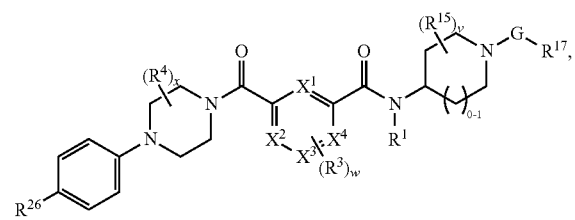

in which $R^{26}$ is trifluoromethyl, chloro, fluoro or cyano and all other variables are as described above with reference to structural formulae (XVIII), (XIX) and (XX).

In certain embodiments, the presently disclosed compounds have the structural formula (XXIV):

(XXIV)

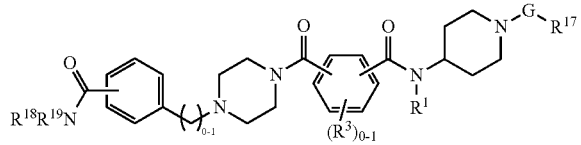

in which G, $R^1$, $R^3$ and $R^{17}$ are as described above with reference to any of structural formulae (I)-(XXIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

For example, in one embodiment, the presently disclosed compounds have the structural formula (XXV):

(XXV)

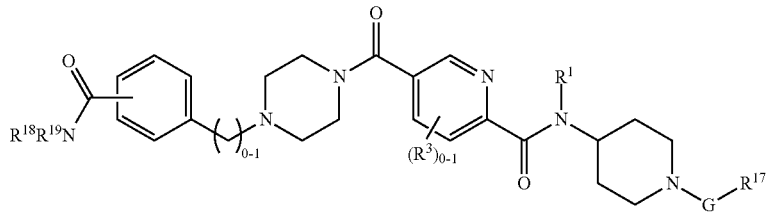

in which G, $R^1$, $R^3$ and $R^{17}$ are as described above with reference to any of structural formulae (I), (VIII), (XIII), (XIV), (XVI) or (XXII), and $R^{18}$ and $R^{19}$ are defined as described above with reference to structural formula (XXIV).

In certain embodiments, the presently disclosed compounds have the structural formula (XXVI):

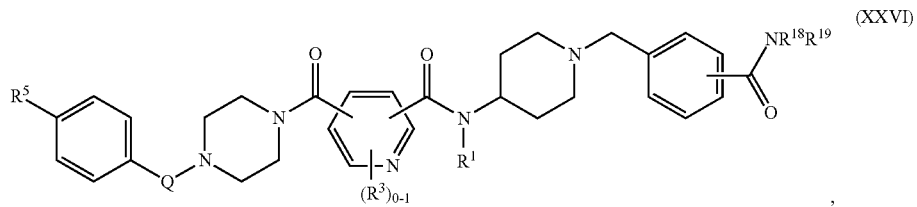
(XXVI)

in which Q, $R^1$, $R^3$ and $R^5$ are defined as described above with reference to any of structural formulae (I)-(XXIII), and $R^{18}$ and $R^{19}$ are defined as described above with reference to structural formula (XXIV).

For example, in one embodiment, the presently disclosed compounds have the structural formula (XXVII):

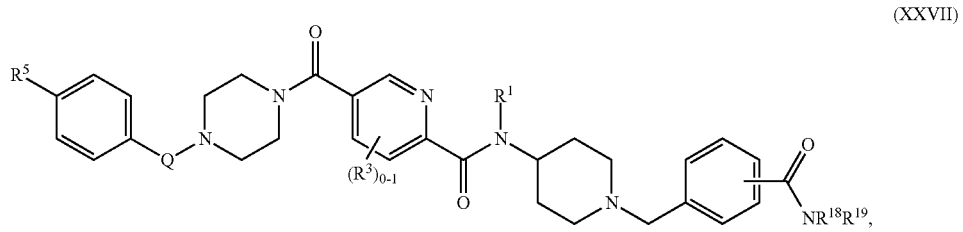
(XXVII)

in which Q, $R^1$, $R^3$ and $R^5$ are defined as described above with reference to any of structural formulae (I)-(XXIII), and $R^{18}$ and $R^{19}$ are defined as described above with reference to structural formula (XXIV).

In certain embodiments, the presently disclosed compounds have the structural formula (XXVIII):

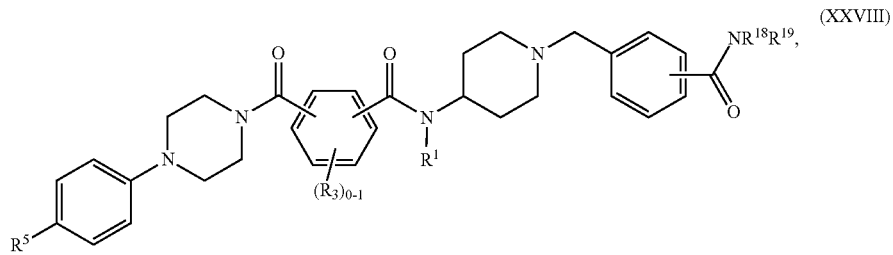
(XXVIII)

in which $R^1$, $R^3$ and $R^5$ are defined as described above with reference to any of structural formulae (I)-(XXIII), and $R^{18}$ and $R^{19}$ are defined as described above with reference to structural formula (XXIV).

For example, in one embodiment, the presently disclosed compounds have the structural formula (XXIX):

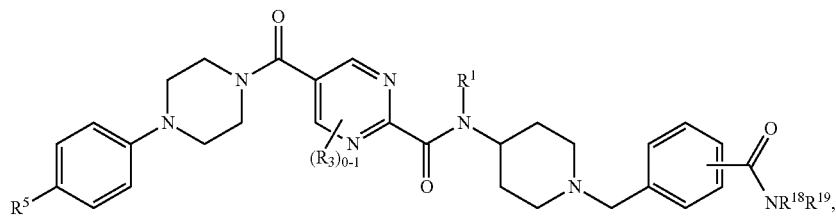

(XXIX)

in which $R^1$, $R^3$ and $R^5$ are defined as described above with reference to any of structural formulae (I)-(XXIII), and $R^{18}$ and $R^{19}$ are defined as described above with reference to structural formula (XXIV).

In compounds according to any of structural formulae (I)-(VII), T and $R^2$ can be defined as described above with reference to structural formulae (VIII)-(XXIX).

In certain embodiments, the presently disclosed compounds have the structural formula (XXX):

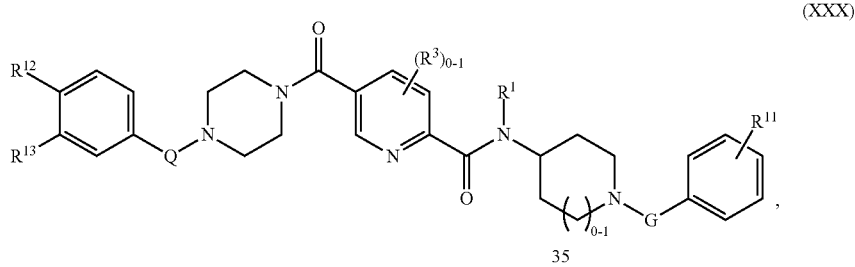

(XXX)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I), (II), and (VIII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

In certain embodiments, the presently disclosed compounds have the structural formula (XXXI):

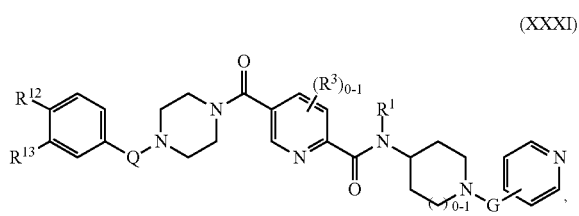

(XXXI)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I), (II) and (VIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

In certain embodiments, the presently disclosed compounds have the structural formula (XXXII):

(XXXII)

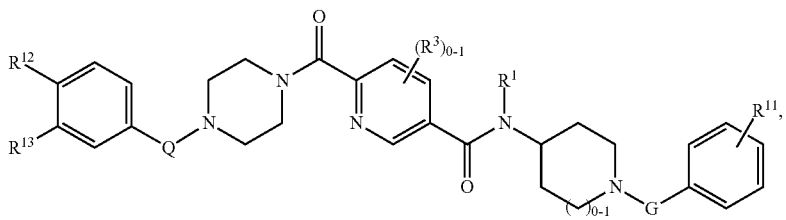

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I), (III), and (VIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (XXXIII):

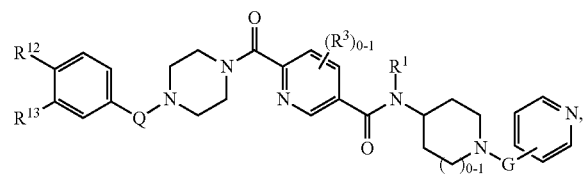

(XXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I), (III) and (VIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (XXXIV):

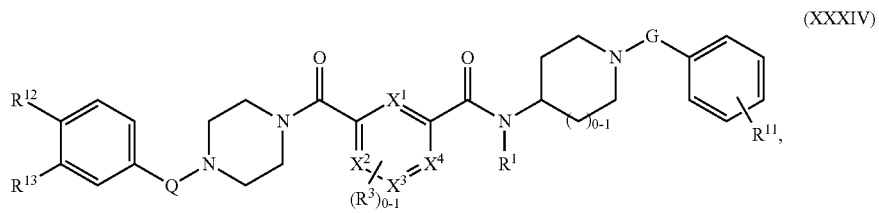

(XXXIV)

in which one of X$^1$, X$^2$, X$^3$ and X$^4$ are N, and the others are carbons (for example, independently CH or C substituted with one of the w R$^3$ groups), as described above with reference to structural formulae (IV) and (VII); Q is —CH$_{2-5}$—C(O)— or a single bond; G is a single bond, —CH$_2$—, —C(O)—, —S(O)$_2$— or —C(O)—NH—; R$^1$ and R$^3$ are as described above with reference to any of structural formulae (I), (IV), and (VIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (XXXV):

(XXXV)

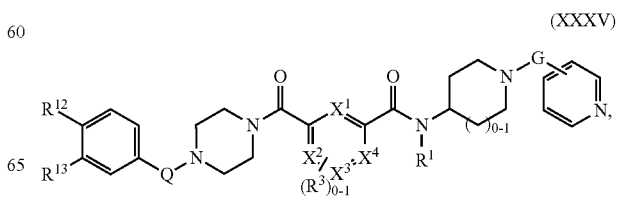

in which one of $X^1$, $X^2$, $X^3$ and $X^4$ are N, and the others are carbons (for example, independently CH or C substituted with one of the w $R^3$ groups), as described above with reference to structural formulae (IV) and (VII); Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (I), (IV) and (VIII); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central pyridine. In another embodiment, one $R^3$ (e.g., —Cl, —F, —CH$_3$, —C$_2$H$_5$, —C$_3$H$_7$) is substituted on the central pyridine.

In one embodiment of the presently disclosed compounds of any of structural formulae (I)-(XXXV), the compound has the structural formula (VIII), in which the "A" ring system is an aryl or heteroaryl; and in which the compound has a computed low energy three-dimensional conformer in which the oxygen of the —C(O)—NR$^1$— group is positioned at (0 Å, 0 Å, 0 Å); the centerpoint of the central pyridine is positioned within 3.5 Å of (−3.1 Å, 0.4 Å, 1.2 Å); the nitrogen of the right-hand azacycloalkyl (i.e., the ring to which -G-R$^{17}$ is bound) is positioned within 3.5 Å of (0.8 Å, 1.6 Å, −5.3 Å); the centerpoint of the left-hand diazacycloalkyl is positioned within 3.5 Å of (−6.2 Å, 0.1 Å, 7.4 Å); and the centerpoint of an aromatic ring of the aryl or heteroaryl of the "A" ring system is positioned within 3.5 Å of (−7.4 Å, −1.9 Å, 10.7 Å).

In certain embodiments of the presently disclosed compounds of structural formula (VIII), in a computed low energy three-dimensional conformer:
the oxygen of the —C(O)—NR$^1$— group is positioned at (0 Å, 0 Å, 0 Å);
the centerpoint of the central pyridine is positioned within 2.5 Å of (−3.1 Å, 0.4 Å, 1.2 Å);
the nitrogen of the right-hand azacycloalkyl is positioned within 1.8 Å of (0.8 Å, 1.6 Å, −5.3 Å);
the centerpoint of the left-hand diazacycloalkyl is positioned within 2.5 Å of (−6.2 Å, 0.1 Å, 7.4 Å); and
the centerpoint of an aromatic ring of the aryl or heteroaryl of the "A" ring system is positioned within 2.5 Å of (−7.4 Å, −1.9 Å, 10.7 Å).

In one embodiment of the presently disclosed compounds of structural formula (VIII), the "A" ring system is an aryl or heteroaryl substituted with a hydrophobic moiety; $R^{17}$ is substituted with an electron acceptor; and the compound has a computed low energy three-dimensional conformer in which
the oxygen of the —C(O)—NR$^1$— group is positioned at (0 Å, 0 Å, 0 Å);
the centerpoint of the central pyridine is positioned within 3.5 Å of (−3.1 Å, 0.4 Å, 1.2 Å);
the nitrogen of the right-hand azacycloalkyl is positioned within 3.5 Å of (0.8 Å, 1.6 Å, −5.3 Å);
the centerpoint of the left-hand diazacycloalkyl is positioned within 3.5 Å of (−6.2 Å, 0.1 Å, 7.4 Å);
the centerpoint of an aromatic ring of the aryl or heteroaryl of the "A" ring system is positioned within 3.5 Å of (−7.4 Å, −1.9 Å, 10.7 Å);
the hydrophobic moiety substituted on the "A" ring system is positioned within 3.5 Å of (−9.0 Å, −3.2 Å, 13.4 Å); and
the electron acceptor substituted on $R^{17}$ is positioned within 3.5 Å of (7.0 Å, −2.7 Å, −7.0 Å).

The hydrophobic moiety can be, for example, any of the following, as defined in SMARTS query format:
INCLUDE
[a]F group(2)
[a]Cl group(2)
[a]Br group(2)
[a]I group(2)
[a]C(F)(F)(F) group(2,3,4,5)
[a][CH2]C(F)(F)(F) group(2,3,4,5,6)
[a]O[CH3] group(2,3)
[a]S[CH3] group(2,3)
[a]OC(F)(F)(F) group(2,3,4,5,6)
C(F)(F)(F) group
F group
Cl group
Br group
I group
default aromatic surface group
default aliphatic surface group
C[S;X2]C group
[S;X2]CC group
[S;X2]C group.

The electron acceptor can be, for example, any of the following, as defined in SMARTS query format:
INCLUDE
[N;X1]#[#6] vector(1)
[N;X1]#CC vector(1)
[N;X2](=C~[C,c])C vector(1)
[N;X2](O)=N[a] vector(1)
[N;X2](=N—O)[a] vector(1)
[n;X2]1ccccc1 vector(1)
[n;X2]([a])([a]) vector(1)
[N;X2](=C~[C,c])(~[*]) vector(1)
[N;X3](C)(C)[N;X3]C vector(1)
[N;X2](=C)(~[*]) vector(1)
[N;X2](~[C,c])=[N;X2] vector(1)
[n;X2]1c[nH]cc1 vector(1)
O=[S;X4](=O)([!#8])([!#8]) vector(1)
[O;X2]C vector(1)
[O;X2]N vector(1)
[O;X1]=[C,c] vector(1)
o vector(1)
[O;X2](C)C vector(1)
[O;X2]c1nccccc1 vector(1)
[O;X2]~[a] vector(1)
O=PO([!#1]) vector(1)
[O;X2] vector(1)
[S;X2](C)C vector(1)
[S;X2](=C)N vector(1)
EXCLUDE
O=C[O—,OH] point
[O—,OH]C(=O) point
[nH]([a])[a] point
[#7;X3][*]=[O,S] point
[N;X3](C)(C)[C;X3] point
[N;X3][a] point
N(=N=N)[#6] point
[NH2](C(=O)[NH2]) point
[NH](C=O)(C=O) point

[NH2](S(=O)(=O)[#6])[#6] point
[NH](S(=O)(=O)[#6])[#6] point
n1c([NH2])ccnc1([NH2]) point
o1nccc1 point
o1cncc1 point
o1cccc1 point
[O;X2]C=O point
[O;X2] point.

In one embodiment of the presently disclosed compounds of structural formula (XXII), the "A" ring system is an aryl or heteroaryl substituted with a hydrophobic moiety; $R^{17}$ is substituted with an electron acceptor; and the compound has a computed low energy three-dimensional conformer in which the oxygen of the —C(O)—$NR^1$— group is positioned at (0 Å, 0 Å, 0 Å);
the centerpoint of the central pyridine is positioned within 2.5 Å of (−3.1 Å, 0.4 Å, 1.2 Å);
the nitrogen of the right-hand azacycloalkyl is positioned within 1.8 Å of (0.8 Å, 1.6 Å, −5.3 Å);
the centerpoint of the left-hand diazacycloalkyl is positioned within 2.5 Å of (−6.2 Å, 0.1 Å, 7.4 Å); and
the centerpoint of an aromatic ring of the aryl or heteroaryl of the "A" ring system is positioned within 2.5 Å of (−7.4 Å, −1.9 Å, 10.7 Å);
the hydrophobic moiety substituted on the "A" ring system is positioned within 2.5 Å of (−9.0 Å, −3.2 Å, 13.4 Å); and
the electron acceptor substituted on $R^{17}$ is positioned within 2 Å of (7.0 Å, −2.7 Å, −7.0 Å).

In certain embodiments of the presently disclosed compounds, the computed low energy three-dimensional conformer has a root mean square deviation from the given points of no greater than 3 Å, and a vector score greater than 0.2.

In certain embodiments of the presently disclosed compounds, the computed low energy three-dimensional conformer has a root mean square deviation from the given points of no greater than 1.5 Å, and a vector score greater than 0.4.

In certain embodiments of the presently disclosed compounds, the computed low energy three-dimensional conformer has a root mean square deviation from the given points of no greater than 1.2 Å, and a vector score greater than 0.5.

A centerpoint of a carbocyclic or heterocyclic ring is the average position of the constituent atoms of the ring (i.e., excluding any substituents) as positioned in the low energy three-dimensional conformer. For example, the centerpoint of the left-hand azacycloalkyl is the average position of its ring carbon and nitrogen atom(s). Similarly, the centerpoint of a phenyl ring is the average position of its six ring carbons. Centerpoints are calculated only on single rings; multi-ring systems have multiple centerpoints, one for each ring. For example, a benzofuran would have two centerpoints, one calculated as the average position of the six carbon rings making up the fused benzene subunit, and the other calculated as the average position of the four carbon atoms and one oxygen atom making up the fused furan subunit.

Low energy three-dimensional conformers can be calculated using the Phase software package version 3.0, available from Schrödinger LLC. Low energy three-dimensional conformers can be generated by a torsion search procedure under OPLS_2005 force field with a distance dependent dielectric constant. As the person of skill in the art will appreciate, the low energy conformer should be translated and rotated so that the oxygen of the —C(O)— group is positioned at (0 Å, 0 Å, 0 Å), and so that the root mean square deviation of the rest of the listed features with respect to the given points is minimized.

As the person of skill in the art will recognize, the various embodiments described above can be combined to form other embodiments of the disclosure. For example, in one embodiment, Q is —$CH_2$—, as described above, and G is —$CH_2$—, as described above.

Examples of compounds according to structural formula (I) include those listed in Table 1. These compounds can be made according to the general schemes described below, for example using procedures analogous to those described below in the Examples.

TABLE 1

| No. | Name | Structure |
| --- | --- | --- |
| 1 | 5-(4-(4-cyanobenzyl)piperazine-1-carbonyl)-N-(1-(4-cyanobenzyl)-piperidin-4-yl)picolinamide | 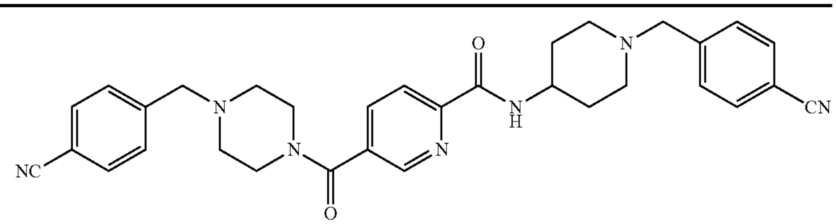 |
| 2 | N-(1-(4-cyanobenzyl)piperidin-4-yl)-5-(4-(4-fluorobenzyl)piperazine-1-carbonyl)picolinamide | 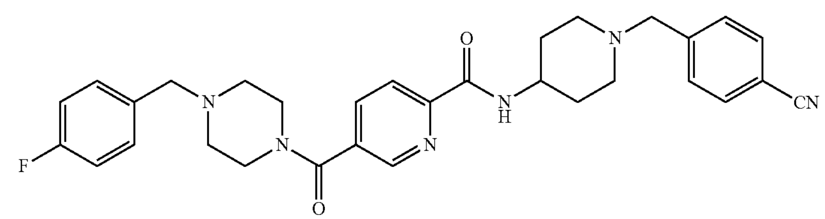 [SMILES: N#Cc1ccc(CN2CCC(NC(=O)c3ccc(C(=O)N4CCN(Cc5ccc(F)cc5)CC4)cn3)CC2)cc1] |
| 3 | N-(1-(4-cyanobenzyl)piperidin-4-yl)-5-(4-(4-(trifluoromethyl)benzyl)piperazine-1-carbonyl)picolinamide | 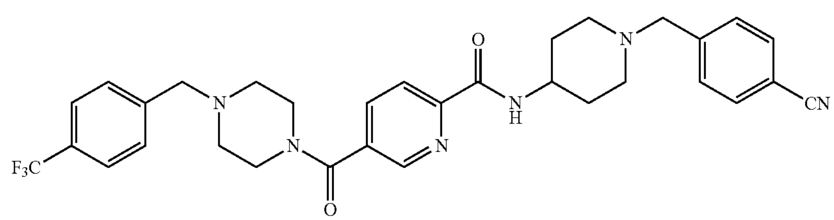 [SMILES: N#Cc1ccc(CN2CCC(NC(=O)c3ccc(C(=O)N4CCN(Cc5ccc(C(F)(F)F)cc5)CC4)cn3)CC2)cc1] |

TABLE 1-continued

| No. | Name |
|---|---|
| 4 | (S)-5-(4-(4-chlorophenyl)piperazine-1-carbonyl)-N-(1-(4-fluorobenzyl)-pyrrolidin-3-yl)picolinamide |
| 5 | (S)-5-(4-(4-chlorophenyl)piperazine-1-carbonyl)-N-(1-(pyridin-4-ylmethyl)pyrrolidin-3-yl)picolinamide |
| 6 | (S)-5-(4-(4-chlorophenyl)piperazine-1-carbonyl)-N-(1-(4-cyanobenzyl)-pyrrolidin-3-yl)picolinamide |
| 7 | N-(1-(4-chlorobenzyl)pyrrolidin-3-yl)-5-(4-(4-chlorophenyl)piperazine-1-carbonyl)picolinamide |
| 8 | 5-(4-(4-chlorophenyl)piperazine-1-carbonyl)-N-(1-(4-(trifluoromethyl)benzyl)pyrrolidin-3-yl)picolinamide |

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, desirably from 1 to about 12 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic carbocyclic ring system having a single ring (e.g., phenyl) which is optionally fused to other aromatic hydrocarbon rings or non-aromatic hydrocarbon rings. "Aryl" includes ring systems having multiple condensed rings and in which at least one is aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —O$^-$M$^+$, =O, —OR$^{70}$, —SR$^{70}$, —S$^-$M$^+$, =S, —NR$^{80}$R$^{80}$, =NR$^{70}$, =N—OR$^{70}$, trihalomethyl, —CF$_3$, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$. Each R$^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$R$^{71}$, —OSO$_2$R$^{71}$, —OSO$_2$O$^-$M$^+$, —OSO$_2$R$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$) NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2^-$M$^+$, —NR$^{71}$CO$_2$R$^{71}$, —NR$^{71}$C(S) OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O) (OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S) OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each R$^{72}$ is independently hydrogen, ($C_1$-$C_6$ alkyl) or ($C_1$-$C_6$ fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)R$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)

$R^{70}$ and $—NR^{70}C(NR^{70})NR^{80}R^{80}$, where $R^{60}$, $R^{70}$, $R^{80}$ and $M^+$ are as previously defined. Substituent groups for hydrogens on nitrogen atoms in "substituted" heteroalkyl and heterocycloalkyl groups are, unless otherwise specified, $—R^{60}$, $—O^-M^+$, $—OR^{70}$, $—SR^{70}$, $—S^-M^+$, $—NR^{80}R^{80}$, trihalomethyl, $—CF_3$, $—CN$, $—NO$, $—NO_2$, $—S(O)_2R^{70}$, $—S(O)_2O^-M^+$, $—S(O)_2OR^{70}$, $—OS(O)_2R^{70}$, $—OS(O)_2O^-M^+$, $—OS(O)_2OR^{70}$, $—P(O)(O^-)_2(M^+)_2$, $—P(O)(OR^{70})O^-M^+$, $—P(O)(OR^{70})(OR^{70})$, $—C(O)R^{70}$, $—C(S)R^{70}$, $—C(NR^{70})R^{70}$, $—C(O)OR^{70}$, $—C(S)OR^{70}$, $—C(O)NR^{80}R^{80}$, $—(NR^{70})NR^{80}R^{80}$, $—OC(O)R^{70}$, $—OC(S)R^{70}$, $—OC(O)OR^{70}$, $—OC(S)OR^{70}$, $—NR^{70}C(O)R^{70}$, $—NR^{70}C(S)R^{70}$, $—NR^{70}C(O)OR^{70}$, $—NR^{70}C(S)OR^{70}$, $—NR^{70}C(O)NR^{80}R^{80}$, $—NR^{70}C(NR^{70})R^{70}$ and $—NR^{70}C(NR^{70})NR^{80}R^{80}$, where $R^{60}$, $R^{70}$, $R^{80}$ and $M^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, 1, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds of structural formulae (I)-(XXXV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(XXXV).

In the pharmaceutical compositions disclosed herein, one or more compounds of structural formulae (I)-(XXXV) may be present in association with one or more pharmaceutically acceptable carriers, diluents or excipients, and, if desired, other active ingredients. The pharmaceutical compositions containing compounds of structural formulae (I)-(XXXV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(XXXV) can be formulated into lotions, oils or powders for application to the skin according to certain methods described below.

Compounds of structural formulae (I)-(XXXV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(XXXV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described herein. For example, compounds of structural formula (I) can be prepared according to Scheme 1, below, or analogous synthetic schemes:

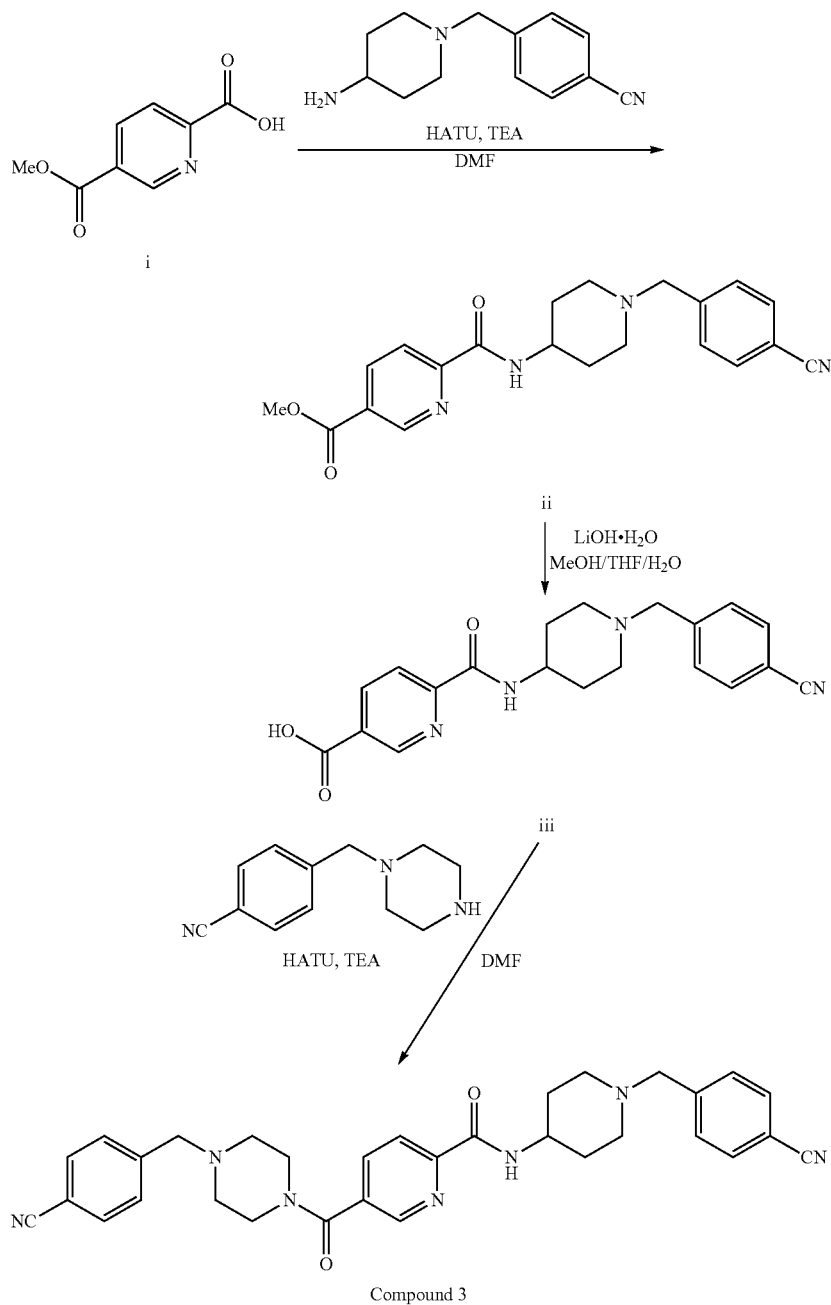

Scheme 1

Referring to Scheme 1, pyridinedicarboxylic acid monomethyl ester (i), for example, is coupled with an amine (here a substituted 1-benzylpiperidine-4-amine) to form a carboxymethyl-substituted pyridinecarboxamide (ii). The ester is saponified and protonated to form the corresponding carboxylic acid (iii), which is then coupled with a suitable amine (in this case, a substituted 1-benzylpiperazine-4-amine) to form Compound 3 of Table 1.

One of skill in the art can adapt the reaction sequences of Schemes 1-5 to fit the desired target molecule. Of course, in certain situat For example, in one particular embodiment, a labeled conjugate has structural formula (XXXVII):

ions one of skill in the art will use different reagents to affect one or more of the individual steps or to use protected versions of certain of the substituents. Additionally, one skilled in the art would recognize that compounds of structural formulae (I)-(XXXV) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

While not intending to be bound by theory, the inventors surmise that compounds of structural formulae (I)-(XXXV)

are mimics of adiponectin which act as adiponectin receptor agonists, thereby activating the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(XXXV) should also inhibit the inflammatory processes which occur during the early phases of atherosclerosis. Accordingly, compounds of structural formulae (I)-(XXXV) can be useful in the treatment of type II diabetes and in the treatment and prevention of atherosclerosis, cardiovascular disease, obesity and non-alcoholic fatty liver disease.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, prodrug, N-oxide (or solvate or hydrate thereof) or composition described above.

In one embodiment, a method of increasing fatty acid oxidation in a cell includes contacting the cell with an effective amount of a compound, pharmaceutically acceptable salt, prodrug, N-oxide (or solvate or hydrate thereof) or composition described above. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, prodrug, N-oxide (or solvate or hydrate thereof) or composition described above.

In another embodiment, a method of increasing glucose uptake in a cell includes contacting the cell with an effective amount of a compound, pharmaceutically acceptable salt, prodrug, N-oxide (or solvate or hydrate thereof) or composition described above.

In another embodiment, a method of reducing triglyceride levels in a subject includes administering to the subject an effective amount of a compound, pharmaceutically acceptable salt, prodrug, N-oxide (or solvate or hydrate thereof) or composition described above.

In another embodiment, a method of increasing insulin sensitivity of a subject includes administering to the subject an effective amount of a compound, pharmaceutically acceptable salt prodrug, N-oxide (or solvate or hydrate thereof) or composition described above.

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, prodrug, solvate, hydrate, N-oxide or composition described above. In another embodiment, a method of treating or preventing atherosclerosis or cardiovascular disease in a subject includes administering to the subject an effective amount of a compound, pharmaceutically acceptable salt, prodrug prodrug, N-oxide (or solvate or hydrate thereof) or composition described above.

As described above, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, prodrug, N-oxide (or solvate or hydrate thereof) or composition described above, or administering a compound, pharmaceutically acceptable salt, prodrug, N-oxide (or solvate or hydrate thereof) or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

In certain embodiments, the compounds disclosed herein affect lipid signaling pathways. For example, in some embodiments, the compounds up-regulate ceramidase activity. Ceramide is a central player in sphingolipid metabolism, and is the immediate precursor of sphingomyelins and glycosphingolipids as well as the bioactive products sphingosine and sphingosine-1-phosphate. Moreover, endogenous ceramide itself mediates, at least in part, the actions of a variety of stimuli on cell differentiation, apoptosis, and growth suppression. Ceramide is deacylated by ceramidase to form sphingosine, which is in turn phosphorylated to sphingosine-1-phosphate by sphingosine kinase.

Elevated ceramide levels have been shown to induce cell apoptosis, differentiation and senescence. Moreover, elevated ceramide levels are linked to a variety of diseases and disorders, including, for example, Batten's disease, inflammatory bowel diseases, diffuse intravascular coagulation, fever, protein catabolism and/or lipid depletion, hepatosplenomegaly associated with inflammatory or metabolic liver diseases, endomyocarditis, endolithial cell and leucocyte activation, capillary thrombosis, meningo-encephalitis due to infectious agents, complications in organ transplantation, rheumatoid arthritis and connective tissue diseases, autoimmune diseases, hyperthyroidism, damage by radiation/chemotherapy agents and chronic fatigue syndrome.

Up-regulating ceramidase function (and therefore reducing the concentration of ceramide) can be used to treat disorders involving deficient cell proliferation (growth) or in which cell proliferation is otherwise desired, for example, degenerative disorders, growth deficiencies, lesions, physical trauma, and diseases in which ceramide accumulates within cells, such as Fabry disease. Other disorders that may benefit from the activation of ceramidase include neurodegenerative disorders such as Alzheimer's disease and amyotrophic lateral sclerosis and disorders of aging such as immune dysfunction, as well as disorders, such as those listed above, linked to elevated ceramide levels.

The compounds, salts, prodrugs, N-oxides, solvates and hydrates described herein can be administered, for example, to a mammalian host to retard cellular responses associated with the activation of the ceramide-mediated signal transduction pathway. The compounds can be useful, for example, in providing protection against cell senescence or apoptosis, such as occurs as a result of trauma (e.g., radiation dermatitis) and aging (e.g., of the skin or other organs).

Another embodiment is a method for up-regulating ceramidase function in a cell (either in vivo or in vitro), the method including contacting the cell with an effective amount of a compound, pharmaceutically acceptable salt, prodrug, N-oxide (or solvate or hydrate thereof) or composition described above.

In another embodiment, a method for decreasing ceramide concentration in a cell (either in vivo or in vitro) includes contacting the cell with an effective amount of a compound, pharmaceutically acceptable salt, prodrug, N-oxide (or solvate or hydrate thereof) or composition described above.

In another embodiment, a method for inhibiting ceramide-activated responses to stimuli in a cell (either in vivo or in vitro) includes contacting the cell with an effective amount of a compound, pharmaceutically acceptable salt, prodrug, N-oxide (or solvate or hydrate thereof) or composition described above. The stimuli can be, for example, stimuli for cell senescence and/or apoptosis.

Another embodiment is a method for treating or preventing a disease or disorder in which cell proliferation is deficient or desired in a subject, the method including administering to the subject an effective amount of a compound, pharmaceutically acceptable salt, prodrug, N-oxide (or solvate or hydrate thereof) or composition described above. Various applicable diseases and disorders are described above.

Another embodiment is a method for treating a disease or disorder linked to elevated ceramide levels in a subject, the method including administering to the subject an effective amount of a compound, pharmaceutically acceptable salt, prodrug, N-oxide (or solvate or hydrate thereof) or composition as described herein. Various applicable diseases and disorders are described above. In certain embodiments, the subject has a ceramide level higher than about 50 pmol/$10^6$ cells.

Moreover, since some drugs can induce high levels of ceramide, the compounds, salts, prodrugs, N-oxides, solvates and hydrates described herein can be usefully co-administered with such drugs in order to at least partially ameliorate this effect. For example, in certain embodiments, an effective amount of a compound, pharmaceutically acceptable salt, prodrug, N-oxide (or solvate or hydrate thereof) or composition as described herein is co-administered with a corticosteroid (e.g., dexamethasone), an anti-inflammatory (e.g., indomethacin), an antiviral (e.g., interfereon), an immunosuppressant (e.g., cyclosporin), a chemotherapy agent (e.g., adriamicin), and immunopotentiant (e.g., an immunoglobulin or a vaccine), or an andocrinological agent (e.g., metimazole). As the person of skill in the art will appreciate, co-administration contemplates not only administration at the same time, but also administration at different times, but with time-overlapping pharmacological effects.

Another embodiment is a method for reducing the effect of aging in the skin of a subject, the method including contacting the skin with a compound, pharmaceutically acceptable salt, prodrug, N-oxide (or solvate or hydrate thereof) or composition as described herein.

Another embodiment is a method for treating or preventing radiation dermatitis in the skin of a subject, the method including contacting the skin with a compound, pharmaceutically acceptable salt, prodrug, N-oxide (or solvate or hydrate thereof) or composition as described herein.

To identify and select therapeutic compounds for use in treating ceramide-associated conditions, cells (or intracellular components such as microsomes) which have not been exposed to a senescence or apoptosis-inducing agent (e.g., cytokines such as TNF-α or exogenous stimuli such as heat, radiation or chemical agents) are exposed to such and agent and to the candidate compound. Inhibition of senescence or apoptosis is measured as a function of cell growth. The person of ordinary skill in the art will be familiar with techniques for obtaining such measurements.

For example, inhibition of cell senescence can be measured after serum deprivation in serum-dependent cells. Many cell types are dependent upon serum factors for growth. Thus, deprivation of such cells of serum provides a model for assessment of compounds to modulate cell responses to intracellular ceramide-mediated signal transduction. In particular, withdrawal of serum from serum-dependent cell cultures produces increased intracellular levels of endogenous ceramide and may also increase intracellular levels of endogenous diacyl glycerol (see, e.g., Jayadev, et al., J. Biol. Chem., 270, 2047-2052 (1995)). To evaluate the inhibitory effect of the compounds described herein on ceramide-associated conditions in vitro, the serum withdrawal model can be used. Specifically, 3T3 fibroblast cells can be seeded in 96 well microtiter plates in DMEM in the presence of 10% fetal bovine serum. The cells are incubated to 90% confluence. The medium is removed, and the cells washed and reincubated in serum-free DMEM. A test compound at a variety of concentrations (e.g., 0, 4, 40 or 400 μM) and cell permeable ceramide (e.g., 0, 5 or 10 μM) are added to the wells. After 24 hrs. incubation, 0.5 μCi of [$^3$H] thymidine is added to each well for 2 hrs. DNA synthesis in the tested cell population is assessed by conventional techniques for detection of [$^3$H] thymidine incorporation. The results of this assay can be used to establish the cell senescence inhibitory efficacy of the test compound.

Inhibition of cell apoptosis can be determined, for example, using CD95 stimulation. Engagement of cell surface receptor CD95 (also known as Fas/Apo-1 antigen) triggers cell apoptosis. DX2 is a functional anti-FAS (CD95) antibody which will, on binding of CD95, activate the sphingomyelinase catalysis of sphingomyelin hydrolysis and production of ceramide (see, re DX2, Cifone, et al., J. Exp. Med., 177, 1547-1552 (1993)). Thus, binding of CD95 is a model for conduction of apoptosis via the sphingomyelin signal transduction pathway. To assess the inhibitory effect of the compounds disclosed herein on ceramide-mediated cell apoptosis, human T lymphoblasts (Jurkat) are suspended at $2 \times 10^6$ cells/mL in RPMI-1640 supplemented with insulin, transferrin, selenium and glutamine. After incubation for 2 hrs. at room temperature with a test compound, pentoxifylline or a control compound (Ro-1724), 25 ng/mL of anti-FAS antibody is added to each suspension. After another 2 hrs., cell apoptosis is measured as a function of the number of cells (counted by hemocytometer) that excluded the vital dye erythrosin B. The results of the experiment can be used to establish the apoptosis inhibitory efficacy of the test compound.

To assess the inhibitory effect of the compounds disclosed herein on death of human lymphocytes, human peripheral blood lymphocytes are isolated from normal human blood and depleted of monocytes by adherence to a plastic substrate. Lymphocytes are then cultured in RPMI-1640 medium with 10% autologous plasma at an initial concentration of $2 \times 10^6$ cells/mL. Aliquots of the cell samples are divided and one half of the samples are incubated with a test compound or 6,7-dimethoxy-1(2H)-isoquinoline (Aldrich) for four days. The remaining half of the samples are allowed to rest for four days. Cell viability after four days is determined by erythrosin B dye exclusion in a hemocytometer. The results of the experiment can be used to establish the apoptosis inhibitory efficacy of the test compound on human lymphocytes as compared to untreated lymphocytes.

Ceramide-activated protein kinase (CaPK) is a 97 kDa protein which is exclusively membrane-bound and is believed to serve a role in the sphingomyelin signal transduction pathway. In particular, CaPK is believed to mediate phosphorylation of a peptide derived from the amino acid sequence surrounding Thr.sup.669 of the epidermal growth factor receptor (i.e., amino acids 663-681). This site is also recognized by the mitogen-activated kinase MAP (also known as a family of extracellular signal-regulated kinases). Thus, the effect of the compounds disclosed herein on CaPK activity in cells can be indicative of the effect that the compounds exert on signal transduction in the sphingomyelin pathway. Accordingly, Jurkat cells are suspended at $2 \times 10^6$ cells/mL in RPMI-1640 medium as described above with respect to the cell apoptosis experiment. After incubation for 2 hrs., either a test compound; 20 μM of ceramide or 25 ng/ml of anti-FAS antibody DX2 are added to each suspension and incubated for 15 mins. After centrifugation and washing, the cells were separately homogenized in a dounce homogenizer. Ceramide kinase levels in each test sample can be assayed as described by Liu, et al., J. Biol. Chem., 269, 3047-3052 (1994), which is hereby incorporated by reference herein in its entirety. Briefly, the membrane fraction is isolated from each test sample of treated cell homogenate by ultracentrifugation and run on a 10% PAGE gel. The gel is washed with guanadine-HCl, and renatured in HEPES buffer. Then [$^{32}$P]-ATP is added to the gel and left there for 10 mins. Thereafter, the gel is extensively washed with 5% TCA. Autophosphorylated kinase is detected by autoradiography. The results of this assay can be used to establish the CaPK inhibitory efficacy of the compounds disclosed herein.

Ceramidase activity can be measured in a variety of ways. For example, a sample from a subject or a sample of cells can be assayed in vitro for RNA or protein levels, structure, and/or activity of the expressed ceramidase RNA or protein. Many methods standard in the art can be thus employed, including but not limited to ceramidase enzyme assays.

Cellular ceramide levels can be monitored directly, or by indirectly monitoring the concentrations of a ceramide metabolite in a cell. For example, ceramide levels can be directly measured by isolating peripheral blood lymphocytes from a subject. The cells are centrifuged to remove supernatant, and lipids are removed from the cell pellet. The organic phase containing the ceramide can be assayed using the diacylglycerase kinase assay for phosphorylating the ceramide which is then evidenced by autoradiography. Methods for performing diacylglycerase kinase assays are described, for example, in Cifone, M. G. et al., J. Exp. Med., 180(4), 1547-52 (1993), Jayadev et al., J. Biol. Chem., 270, 2047-2052. (1995), and Perry, D. K. et al, Methods Enzymology, 312, 22-31 (2000), each of which is hereby incorporated by reference in its entirety.

Another embodiment is the use of a compound, pharmaceutically acceptable salt, prodrug, N-oxide (or solvate or hydrate thereof) or composition as described above in the manufacture of a medicament for any of the therapeutic purposes described above. For example, the medicament can be for the reduction of triglyceride levels in a subject, the treatment of type II diabetes in a subject, or the treatment or prevention of atherosclerosis or cardiovascular disease in a subject. In other embodiments, the medicament can be used to reduce the levels of cellular ceramide in a subject, for example in the treatment of Batten's disease.

The compounds disclosed herein can be linked to labeling agents, for example for use in variety of experiments exploring their receptor binding, efficacy and metabolism. Accordingly, another embodiment is a labeled conjugate comprising a compound as disclosed herein covalently linked to a labeling agent, optionally through a linker. Suitable linker and labeling agents will be readily apparent to those of skill in the art upon consideration of the present disclosure. The labeling agent can be, for example, an affinity label such as biotin or strepavidin, a hapten such as digoxigenin, an enzyme such as a peroxidase, or a fluorophoric or chromophoric tag. Any suitable linker can be used. For example, in some embodiments, an ethylene glycol, oligo(ethylene glycol) or poly (ethylene glycol) linker is used. Other examples of linkers include amino acids, which can be used alone or in combination with other linker groups, such as ethylene glycol, oligoethylene glycol or polyethylene glycol. Suitable linkers include, without limitation, single amino acids, as well as di- and tripeptides. In one embodiment, the linker includes a glycine residue. The person of skill in the art will realize, of course, that other linkers and labeling agents can be used. In other embodiments, an alkylene chain is the linker. In other embodiments, the linker has the structure —[(C$_0$-C$_3$ alkyl)-Y$^m$—]$_m$—, in which each Y$^m$ is —O—, —N(R$^9$)—, or L, and m is in the range of 1-40. For example, in certain embodiments, a labeled conjugate has structural formula (XXXVI):

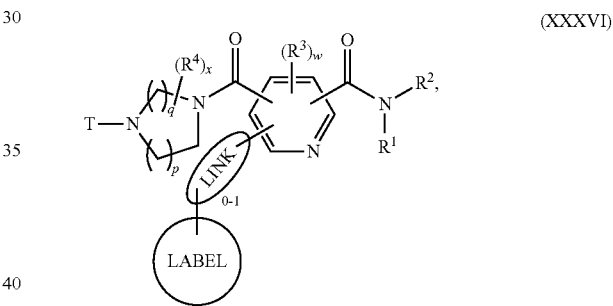

(XXXVI)

in which the "LINK" moiety is a linker and is optional, and the "LABEL" moiety is a labeling agent, and all other variables are as described above, for example with reference to structural formula (I). Any of the compounds disclosed with reference to structural formulae (I)-(XXXV) can be used in the labeled conjugate of structural formula (XXXVI).

For example, in one particular embodiment, a labeled conjugate has structural formula (XXXVII):

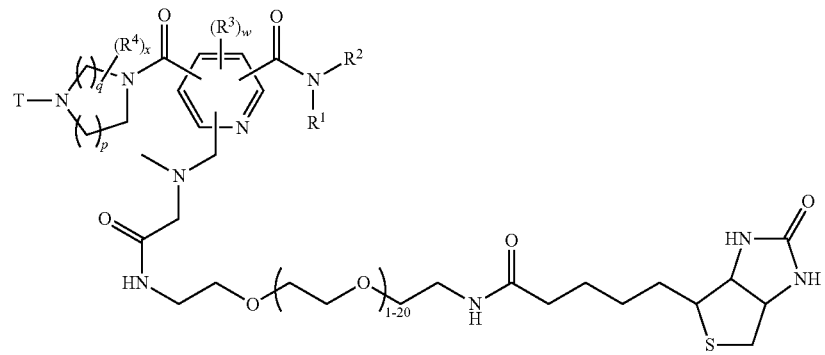

(XXXVII)

in which all variables are as described above, for example with reference to any of structural formulae (I)-(XXXV).

Another disclosed embodiment of a labeled conjugate has the formula (XXXVIII):

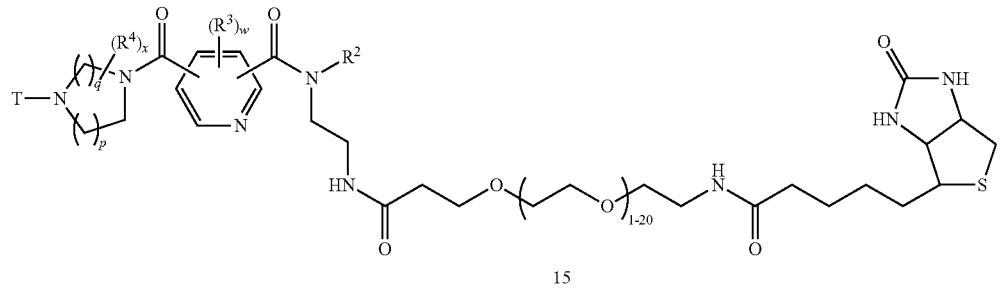

A particular example of a compound according to formula (XXXVIII) has the structure of formula (XXXIX):

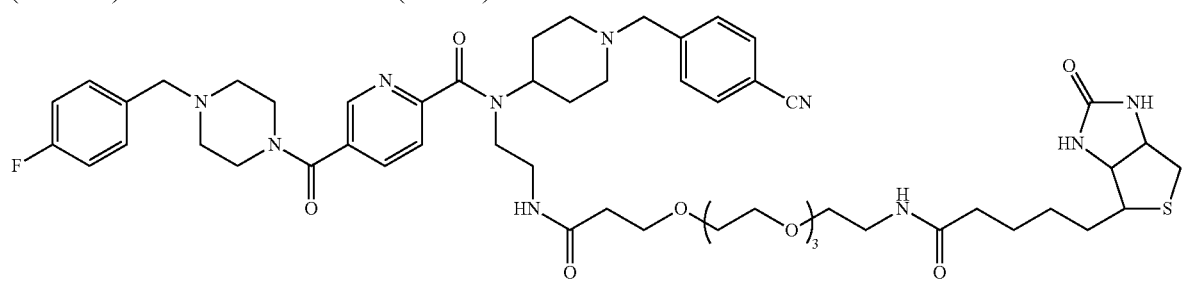

Compounds of formulae (XXXVIII) and (XXXIX) can be synthesized by those of skill in the art of organic synthesis, for example by reductive amination of N-Boc-glycine aldehyde with a primary amine $HNR^2$, for example as illustrated more specifically in Scheme 2:

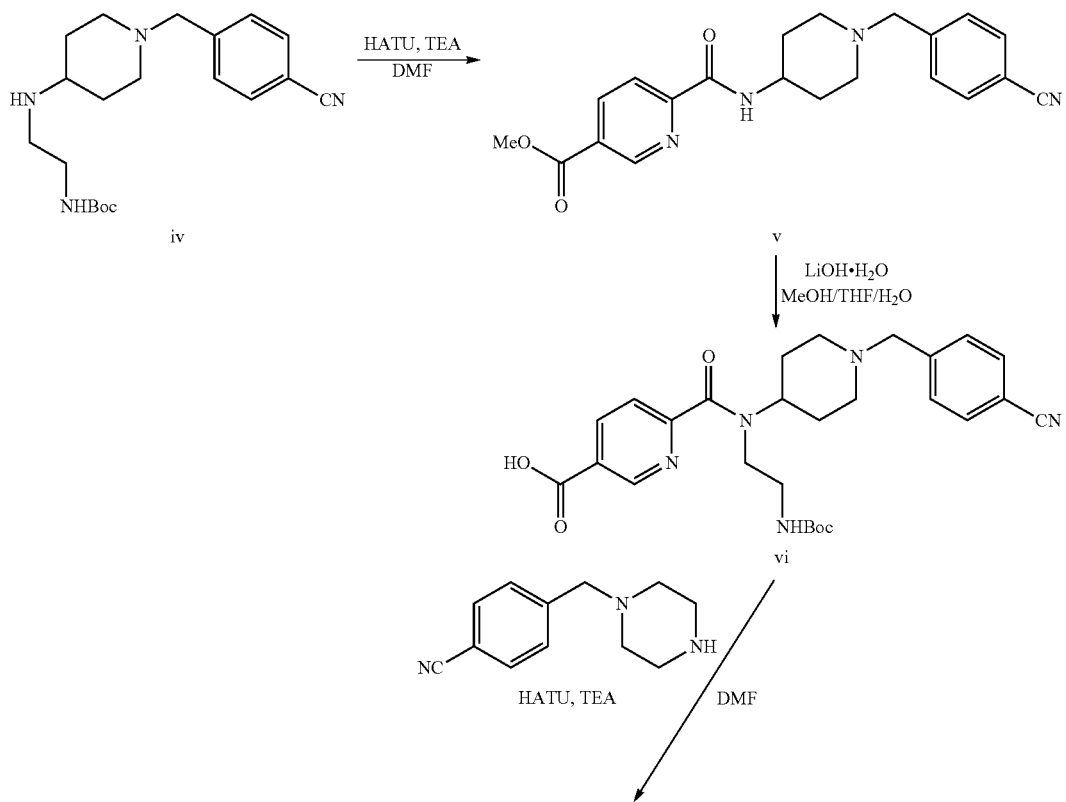

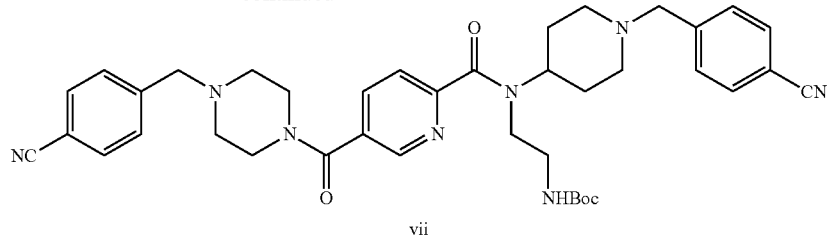

vii

With reference to Scheme 2, reductive amination as is known to those of skill in the art yields intermediate (iv). Intermediate (iv) is acylated according to Scheme 2 to yield intermediate (v), which after saponification and amide bond formation yields intermediate (vii). Intermediate (vii) can be used to produce labeled compound (XXXIX) as is known to those of skill in the art by removal of the Boc group under acidic conditions, followed by acylation with the appropriate commercially available biotin labeling agent.

The following examples are intended to further illustrate certain embodiments and are not intended to limit the scope of the invention.

EXAMPLES

Example 1

The following compounds were made using methods analogous to those of Scheme 1:

Compound 1: 5-(4-(4-cyanobenzyl)piperazine-1-carbonyl)-N-(1-(4-cyanobenzyl)piperidin-4-yl)picolinamide. $^1$H-NMR (CDCl$_3$, 300 MHz): δ 8.396 (s, 1H), 7.8 (d, 2H), 7.65 (m, 2H), 7.621 (d, 2H), 7.47 (dd, 4H), 6.57 (d, 1H), 4.05 (m, 1H), 3.90 (m, 2H), 3.69 (m, 4H), 2.85 (m, 2H), 2.24 (m, 4H), 2.06 (m, 4H); LCMS (m/z): 577 (MH$^+$).

Compound 2: N-(1-(4-cyanobenzyl)piperidin-4-yl)-5-(4-(4-fluorobenzyl)piperazine-1-carbonyl)picolinamide. $^1$H-NMR (CDCl$_3$, 300 MHz): δ 8.56 (s, 1H), 8.19 (d, 2H), 7.88 (d, 1H), 7.85 (m, 1H), 7.63 (d, 2H), 7.27 (d, 2H), 7.27 (m, 2H), 6.99 (d, 2H), 4.05 (m, 1H), 3.81 (m, 2H), 3.74 (s, 2H), 3.52 (s, 2H), 3.38 (m, 2H), 2.99 (m, 2H), 2.55 (m, 2H), 2.40 (m, 4H), 2.07 (m, 2H), 1.81 (m, 2H); LCMS (m/z): 541 (MH$^+$).

Compound 3: N-(1-(4-cyanobenzyl)piperidin-4-yl)-5-(4-(4-(trifluoromethyl)benzyl)piperazine-1-carbonyl)picolinamide. $^1$H-NMR (CDCl$_3$, 300 MHz): δ 8.57 (s, 1H), 8.21 (s, 1H), 8.17 (d, 1H), 8.15 (d, 1H), 7.84 (d, 1H), 7.69 (d, 2H), 7.59 (m, 3H), 7.43 (d, 2H), 4.13 (m, 1H), 4.08 (s, 2H), 3.81 (m, 2H), 3.64 (s, 2H), 3.41 (m, 4H), 2.58 (m, 6H), 2.12 (m, 4H); LCMS (m/z): 591 (MH$^+$).

Compound 4: (S)-5-(4-(4-chlorophenyl)piperazine-1-carbonyl)-N-(1-(4-fluorobenzyl)pyrrolidin-3-yl)picolinamide. $^1$H-NMR (CDCl$_3$, 300 MHz): δ 8.75 (d, 1H), 8.38 (s, 1H), 8.16 (d, 1H), 7.89 (m, 1H), 7.39 (m, 2H), 7.23 (m, 2H), 7.05 (m, 2H), 6.83 (m, 2H), 4.85 (s, 1H), 4.01 (m, 4H), 3.62 (s, 2H), 3.23 (m, 2H), 3.11 (m, 4H), 2.82 (m, 2H), 2.50 (m, 1H), 2.13 (m, 1H); LCMS (m/z): 523 (MH$^+$).

Compound 5: (S)-5-(4-(4-chlorophenyl)piperazine-1-carbonyl)-N-(1-(pyridin-4-ylmethyl)pyrrolidin-3-yl)picolinamide. $^1$H-NMR (CDCl$_3$, 300 MHz): δ 8.62 (m, 2H), 8.52 (d, 1H), 8.21 (m, 2H), 7.89 (m, 1H), 7.23 (m, 2H), 6.83 (m, 2H), 5.42 (m, 4H), 4.79 (s, 1H), 3.93 (m, 2H), 3.55 (m, 2H), 3.25 (m, 2H), 3.04 (m, 2H), 2.71 (m, 2H), 2.49 (m, 1H), 2.01 (m, 1H); LCMS (m/z): 504 (MH$^+$).

Compound 6: (S)-5-(4-(4-chlorophenyl)piperazine-1-carbonyl)-N-(1-(4-cyanobenzyl)pyrrolidin-3-yl)picolinamide. $^1$H-NMR (CDCl$_3$, 300 MHz): δ 8.61 (d, 1H), 8.24 (s, 1H), 8.17 (d, 1H), 7.89 (m, 1H), 7.65 (m, 2H), 7.57 (m, 2H), 7.21 (m, 2H), 6.83 (m, 2H), 4.85 (s, 1H), 4.01 (m, 4H), 3.62 (s, 2H), 3.23 (m, 2H), 3.11 (m, 4H), 2.82 (m, 2H), 2.50 (m, 1H), 2.13 (m, 1H); LCMS (m/z): 530 (MH$^+$).

Compound 7: N-(1-(4-chlorobenzyl)pyrrolidin-3-yl)-5-(4-(4-chlorophenyl)piperazine-1-carbonyl)picolinamide. $^1$H-NMR (CDCl$_3$, 300 MHz): δ 8.76 (d, 1H), 8.33 (s, 1H), 8.17 (d, 1H), 7.89 (m, 1H), 7.37 (m, 4H), 7.22 (m, 2H), 6.83 (m, 2H), 4.87 (s, 1H), 4.05 (m, 4H), 3.47 (s, 2H), 3.28 (m, 2H), 3.15 (m, 4H), 2.86 (m, 2H), 2.51 (m, 1H), 2.19 (m, 1H); LCMS (m/z): 539 (MH$^+$).

Compound 8: 5-(4-(4-chlorophenyl)piperazine-1-carbonyl)-N-(1-(4-(trifluoromethyl)benzyl)pyrrolidin-3-yl)picolinamide. $^1$H-NMR (CDCl$_3$, 300 MHz): δ 8.67 (d, 1H), 8.31 (s, 1H), 8.18 (d, 1H), 7.89 (m, 1H), 7.59 (m, 4H), 7.23 (m, 2H), 6.83 (m, 2H), 4.85 (s, 1H), 4.05 (m, 4H), 3.62 (s, 2H), 3.18 (m, 2H), 3.11 (m, 4H), 2.82 (m, 2H), 2.50 (m, 1H), 2.11 (m, 1H); LCMS (m/z): 573 (MH$^+$).

Example 2

Increase in AMPK Activity

Compounds 1-8 were assayed for their ability to activate AMPK using an enzyme-linked immunosorbent assay. The EC$_{50}$ values for AMPK activation for compounds 1-54 are presented in Table 2 below, in which "A" is less than 0.5 µM; "B" is 0.5-1 µM; "C" is 1-5 µM; and "D" is 5-10 µM; "E" is 10-50 µM; and "F" is >100 µM:

TABLE 2

| Cpd No. | AMPK EC$_{50}$ |
|---|---|
| 1 | A |
| 2 | A |
| 3 | A |
| 4 | C |
| 5 | C |
| 6 | B |
| 7 | C |
| 8 | C |

What is claimed is:

1. A method for reducing triglyceride levels, or treating type II diabetes, atherosclerosis or cardiovascular disease in a subject in need thereof, the method comprising administering to the subject an effective amount of a compound having the structural formula

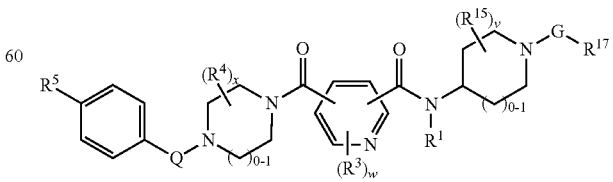

or a pharmaceutically acceptable salt, or N-oxide thereof, wherein $R^1$ is H, —($C_1$-$C_4$ alkyl), —C(O)—($C_1$-$C_4$ alkyl) or —C(O)O—($C_1$-$C_4$ alkyl);

each $R^3$ is independently selected from —($C_1$-$C_3$ alkyl), —($C_1$-$C_3$ haloalkyl), -halogen, —$NO_2$ and —CN;

w is 0, 1 or 2;

each $R^4$ is independently selected from —($C_1$-$C_3$ alkyl), —($C_1$-$C_3$ haloalkyl), -halogen, and two $R^4$ on the same carbon optionally combine to form oxo;

x is 0, 1 or 2;

Q and G are each independently a bond, —$CH_2$—, —C(H)($R^{16}$)—, —C($R^{16}$)$_2$—, —S(O)$_2$—;

v is 0, 1 or 2;

each $R^{15}$ is independently selected from —($C_1$-$C_3$ alkyl), —($C_1$-$C_3$ haloalkyl), -halogen, and two $R^{15}$ on the same carbon optionally combine to form oxo;

$R^{17}$ is phenyl or pyridyl, each optionally substituted with 1, 2 or 3 substituents selected from —($C_1$-$C_3$ alkyl), —($C_1$-$C_3$ haloalkyl), -halogen, —$NO_2$ and —CN, $R^5$ is selected from —($C_1$-$C_3$ alkyl), —($C_1$-$C_3$ haloalkyl), -halogen, —$NO_2$ and —CN;

in which
  each $R^{16}$ is independently selected from —($C_1$-$C_3$ alkyl), and optionally two of $R^{16}$ on the same carbon combine to form oxo.

2. A method according to claim 1, wherein the compound has the structural formula

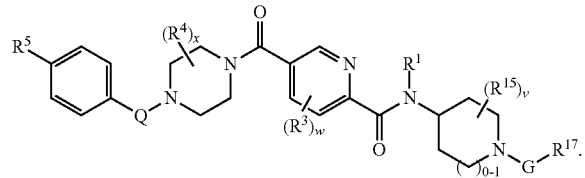

3. A method according to claim 1, wherein the compound has the structural formula

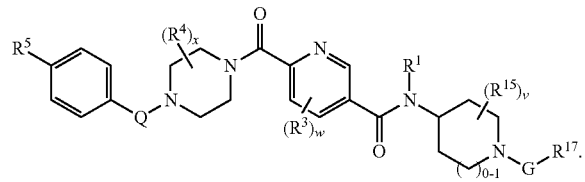

4. A method according to claim 1, wherein the compound has the structural formula

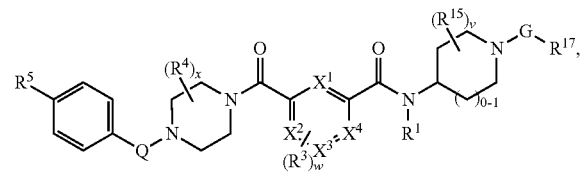

in which one of $X^1$, $X^2$, $X^3$ and $X^4$ is N, and the others are carbons.

5. A method according to claim 1, wherein Q is —$CH_2$—, a single bond, —C(O)—, —S(O)$_2$— or —CH($CH_3$)—.

6. A method according to claim 1, wherein $R^5$ is chloro, fluoro, cyano, trifluoromethyl or $NO_2$.

7. A method according to claim 1, wherein $R^1$ is H.

8. A method according to claim 1, wherein w is 0.

9. A method according to claim 1, wherein w is at least 1, and at least one $R^3$ is selected from the group consisting of halo, cyano, —($C_1$-$C_3$ fluoroalkyl) and $NO_2$.

10. A method according to claim 1, wherein x is 0.

11. A method according to claim 1, wherein two $R^4$ groups combine to form an oxo.

12. A method according to claim 1, wherein the compound has the structural formula

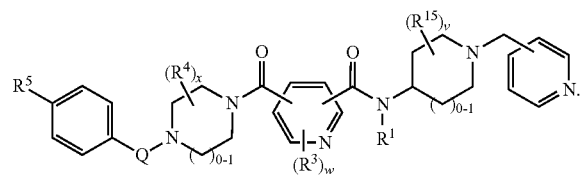

13. A method according to claim 1, wherein the compound has the structural formula

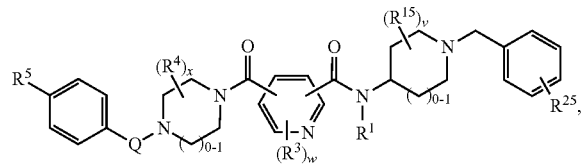

in which $R^{25}$ is selected from halo, cyano, —($C_1$-$C_3$ fluoroalkyl), and $NO_2$.

14. A method according to claim 1, wherein v is 0, w is 0 and x is 0.

15. A method according to claim 1, wherein Q is —$CH_2$— or a single bond.

16. A method according to claim 1, wherein $R^5$ is —Cl, —F, cyano, trifluoromethyl or difluoromethyl.

17. A method according to claim 1, wherein the $R^{17}$ phenyl or pyridyl is optionally substituted with one or two substituents selected from halo, cyano, —($C_1$-$C_3$ fluoroalkyl) and $NO_2$.

18. A method according to claim 1, wherein G is —$CH_2$—; a single bond; —S(O)$_2$—; —C(O)—; or —CH($CH_3$)—.

19. A method according to claim 1, wherein each $R^3$ is halo or —($C_1$-$C_3$ alkyl).

20. A method according to claim 1, wherein
$R^5$ is halo, cyano, —($C_1$-$C_3$ haloalkyl), or $NO_2$;
Q is —$CH_2$—; a single bond; —S(O)$_2$—; —C(O)—; or —CH($CH_3$)—;
x is 0;
w is 0;
$R^1$ is H;
v is 0;
G is —$CH_2$—; a single bond; —S(O)$_2$—; —C(O)—; or —CH($CH_3$)—; and
$R^{17}$ is phenyl or pyridyl, optionally substituted with one or two substituents selected from halo, cyano, —($C_1$-$C_3$ fluoroalkyl), and $NO_2$.

21. A method according to claim 1, wherein G is —$CH_2$—, a single bond, —S(O)$_2$—, —C(O)— or —CH($CH_3$)—; and Q is —$CH_2$—, a single bond, —C(O)—, —S(O)$_2$— or —CH($CH_3$)—.

22. A method according to claim 1, wherein the compound is
5-(4-(4-cyanobenzyl)piperazine-1-carbonyl)-N-(1-(4-cyanobenzyl)piperidin-4-yl)picolinamide;
N-(1-(4-cyanobenzyl)piperidin-4-yl)-5-(4-(4-fluorobenzyl)piperazine-1-carbonyl)picolinamide;
N-(1-(4-cyanobenzyl)piperidin-4-yl)-5-(4-(4-(trifluoromethyl)benzyl)piperazine-1-carbonyl)picolinamide
(S)-5-(4-(4-chlorophenyl)piperazine-1-carbonyl)-N-(1-(4-fluorobenzyl)pyrrolidin-3-yl)picolinamide;
(S)-5-(4-(4-chlorophenyl)piperazine-1-carbonyl)-N-(1-(pyridin-4-ylmethyl)pyrrolidin-3-yl)picolinamide;
(S)-5-(4-(4-chlorophenyl)piperazine-1-carbonyl)-N-(1-(4-cyanobenzyl)pyrrolidin-3-yl)picolinamide;
N-(1-(4-chlorobenzyl)pyrrolidin-3-yl)-5-(4-(4-chlorophenyl)piperazine-1-carbonyl)picolinamide; or 5-(4-(4-chlorophenyl)piperazine-1-carbonyl)-N-(1-(4-(trifluoromethyl)benzyl)pyrrolidin-3-yl)picolinamide.

23. A method according to claim 1, wherein the method is for reducing triglyceride levels in the subject.

24. A method according to claim 1, wherein the method is for treating type II diabetes in the subject.

25. A method according to claim 1, wherein the method is for treating atherosclerosis in the subject.

26. A method according to claim 1, wherein the method is for treating cardiovascular disease in the subject.

27. A method for decreasing ceramide concentration in a cell, the method comprising contacting the cell with an effective amount of a compound having the structural formula

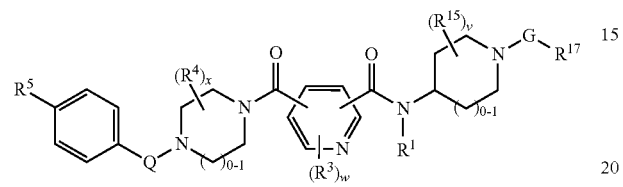

or a pharmaceutically acceptable salt, or N-oxide thereof, wherein $R^1$ is H, —($C_1$-$C_4$ alkyl), —C(O)—($C_1$-$C_4$ alkyl) or —C(O)O—($C_1$-$C_4$ alkyl);

each $R^3$ is independently selected from —($C_1$-$C_3$ alkyl), —($C_1$-$C_3$ haloalkyl), -halogen, —$NO_2$ and —CN;

w is 0, 1 or 2;

each $R^4$ is independently selected from —($C_1$-$C_3$ alkyl), —($C_1$-$C_3$ haloalkyl), -halogen, and two $R^4$ on the same carbon optionally combine to form oxo;

x is 0, 1 or 2;

Q and G are each independently a bond, —$CH_2$—, —C(H)($R^{16}$)—, —C($R^{16}$)$_2$—, —S(O)$_2$—;

v is 0, 1 or 2;

each $R^{15}$ is independently selected from —($C_1$-$C_3$ alkyl), —($C_1$-$C_3$ haloalkyl), -halogen, and two $R^{15}$ on the same carbon optionally combine to form oxo;

$R^{17}$ is phenyl or pyridyl, each optionally substituted with 1, 2 or 3 substituents selected from —($C_1$-$C_3$ alkyl), —($C_1$-$C_3$ haloalkyl), -halogen, —$NO_2$ and —CN, $R^5$ is selected from —($C_1$-$C_3$ alkyl), —($C_1$-$C_3$ haloalkyl), -halogen, —$NO_2$ and —CN;

in which each $R^{16}$ is independently selected from —($C_1$-$C_3$ alkyl), and optionally two of $R^{16}$ on the same carbon combine to form oxo.

* * * * *